(12) United States Patent
Matsuoka et al.

(10) Patent No.: US 9,303,083 B2
(45) Date of Patent: Apr. 5, 2016

(54) THERAPEUTIC AGENT FOR MALIGNANT TUMORS EXPRESSING MHC CLASS II

(75) Inventors: Shuji Matsuoka, Bunkyo-ku (JP); Yasuyuki Ishii, Minoo (JP)

(73) Assignees: RIKEN, Wako-shi (JP); JUNTENDO EDUCATIONAL FOUNDATION, Tokyo (JP)

( * ) Notice: Subject to any disclaimer, the term of this patent is extended or adjusted under 35 U.S.C. 154(b) by 144 days.

(21) Appl. No.: 13/877,844

(22) PCT Filed: Oct. 4, 2011

(86) PCT No.: PCT/JP2011/072897
§ 371 (c)(1),
(2), (4) Date: Apr. 4, 2013

(87) PCT Pub. No.: WO2012/046745
PCT Pub. Date: Apr. 12, 2012

(65) Prior Publication Data
US 2013/0236470 A1 Sep. 12, 2013

(30) Foreign Application Priority Data
Oct. 4, 2010 (JP) ................................. 2010-224632

(51) Int. Cl.
*C07K 16/28* (2006.01)
*C07K 16/18* (2006.01)
*C07K 16/30* (2006.01)

(52) U.S. Cl.
CPC ............. *C07K 16/18* (2013.01); *C07K 16/2803* (2013.01); *C07K 16/30* (2013.01); *C07K 2317/34* (2013.01); *G01N 2333/70539* (2013.01)

(58) Field of Classification Search
None
See application file for complete search history.

(56) References Cited

U.S. PATENT DOCUMENTS

| | | | |
|---|---|---|---|
| 6,416,958 B2 * | 7/2002 | Vidovic et al. | 435/7.1 |
| 7,262,278 B2 * | 8/2007 | Tawara et al. | 530/388.7 |
| 8,128,926 B2 * | 3/2012 | Mi et al. | 424/130.1 |
| 2003/0032782 A1 | 2/2003 | Nagy et al. | |
| 2004/0091974 A1 | 5/2004 | Tawara et al. | |
| 2009/0136526 A1 * | 5/2009 | McDonagh et al. | 424/179.1 |
| 2011/0117602 A1 | 5/2011 | Ito et al. | |

FOREIGN PATENT DOCUMENTS

| | | |
|---|---|---|
| JP | 2004 515214 | 5/2004 |
| WO | 03 033538 | 4/2003 |
| WO | 2009 066655 | 5/2009 |

OTHER PUBLICATIONS

Rudikoff et al. (Proceedings of the National Academy of Sciences, 1982, 79:1979-1983).*
MacCallum et al. (Journal of Molecular Biology, 1996, 262:732-745).*
De Pascalis et al. (Journal of Immunology, 2002, 169:3076-3084).*
Casset et al. (Biochemical and Biophysical Research Communications, 2003, 307:198-205).*
Vajdos et al. (Journal of Molecular Biology, 2002, 320:415-428).*
Holm et al. (Molecular Immunology, 2007:1075-1084).*
Chen et al. (Journal of Molecular Biology, 1999, 293:865-881).*
McLaughlin, P. et al., "Rituximab Chimeric Anti-CD20 Monoclonal Antibody Therapy for Relapsed Indolent Lymphoma: Half of Patients Respond to a Four-Dose Treatment Program,", Journal of Clinical Oncology, vol. 16, No. 8, pp. 2825 to 2833, (Aug. 1998).
Coiffier, B. M.D. et al., "Chop Chemotherapy Plus Rituximab Compared With Chop Alone in Elderly Patients With Diffuse Large-B-Cell Lymphoma," New England Journal of Medicine, vol. 346, No. 4, pp. 235 to 242, (Jan. 24, 2002).
"Emergence of Molecular Target Drug Achieved Breakthrough in therapy of Malignant Lymphoma," October Issue of Cancer Support, pp. 92 to 99, (2005) (with English translation).
International Search Report Issued Dec. 27, 2011 in PCT/JP11/072897 Filed Oct. 4, 2011.

* cited by examiner

*Primary Examiner* — Sean Aeder
*Assistant Examiner* — Julie Wu
(74) *Attorney, Agent, or Firm* — Oblon, McClelland, Maier & Neustadt, L.L.P.

(57) ABSTRACT

Provided is a novel therapeutic agent specific for a malignant tumor expressing MHC class II. The present invention provides an antibody recognizing a protein constituting MHC class II expressed on a malignant tumor, the antibody comprising at least one selected from heavy chain CDR1 (amino acid sequence represented by positions 49 to 54 of SEQ ID NO: 54), heavy chain CDR2 (amino acid sequence represented by positions 69 to 84 of SEQ ID NO: 54), heavy chain CDR3 (amino acid sequence represented by positions 117 to 128 of SEQ ID NO: 54), light chain CDR1 (amino acid sequence represented by positions 46 to 55 of SEQ ID NO: 56), light chain CDR2 (amino acid sequence represented by positions 71 to 77 of SEQ ID NO: 56), and light chain CDR3 (amino acid sequence represented by positions 100 to 108 of SEQ ID NO: 56).

11 Claims, 15 Drawing Sheets

Figure 15

Antibody gene (heavy chain variable region) cloned from 4713 antibody-producing hybridoma

- Heavy chain
  (variable region)

429 bases 143 amino acids

```
               10         20         30         40         50         60
      ATGAGAGTGCTGACTCTGTTTGTGCTGCTTCACAGCCTTCCTACAGCCTTCCTACAGTCCTGTATCCTGTCTTGATGTG
       M  R  V  L  T  L  F  V  L  L  H  S  L  P  T  A  P  P  Q  I  L  D  V 70         80         90        100        110        120
      CAGCTTCAGGAGTCGGGACCTGGCCTGGTGAAACCTTCTCAGTCTCTGTCCCTCACCTGC
       Q  L  Q  E  S  G  P  G  L  V  K  P  S  Q  S  L  S  L  T  C 130        140        150        160        170        180
      ACTGTCACTGGCTACTCAATGATCAATGATTATGCCTGGAACTGGATCCGGCAGTTTCCA
       T  V  T  G  Y  S  M  I  N  D  Y  A  W  N  W  I  R  Q  F  P 190        200        210        220        230        240
      GGAAACAAACTGGAATGGATGGGCTACATAAGCTACAATGATTTCACTTACTACAACCCA
       G  N  K  L  E  W  M  G  Y  I  S  Y  N  D  F  T  Y  Y  N  P 250        260        270        280        290        300
      TCTCTCAAAAGTCGAATCTCCATCACTCGAGACATCTCAAGACCATCTTCCTGCAG
       S  L  K  S  R  I  S  I  T  R  D  T  S  K  N  Q  F  F  L  Q 310        320        330        340        350        360
      TTGAATTCTGTGACTGCCGAGGACACAGCCACTTACTACTGTGTAAGTGAGAGCTTCGC
       L  N  S  V  T  A  E  D  T  A  T  Y  Y  C  V  S  E  R  L  R 370        380        390        400        410        420
      TTAGTAAACATGTTATGGACTACTGGGGTCAGGGAACCTCAGTCATCGTCTCCTCAGCC
       L  V  N  M  D  Y  W  G  Q  G  T  S  V  I  V  S  S  A

430
      AAAACGACA
       K  T  T
```

Figure 16

Antibody gene (light chain variable region) cloned from 4713 antibody-producing hybridoma

- Light chain variable region 396 bases 132 amino acids

THERAPEUTIC AGENT FOR MALIGNANT TUMORS EXPRESSING MHC CLASS II

TECHNICAL FIELD

The present invention relates to an antibody having cytotoxic activity specific for a malignant tumor expressing class II major histocompatibility complex (MHC class II), particularly, malignant lymphoma. The present invention also relates to a pharmaceutical composition and a reagent for detecting malignant lymphoma, comprising the antibody.

BACKGROUND ART

Malignant lymphoma is a tumor that originates from lymphoid tissues. Its types are classified into Hodgkin's lymphoma and non-Hodgkin's lymphoma. The malignant lymphoma is treated mainly by radiotherapy and chemotherapy using anticancer agents. The malignant lymphoma is difficult to cure or may recur, because this tumor can affect the whole body.

In recent years, a chimeric antibody rituximab directed against CD20has been prepared. This antibody exerts significant antitumor effects on B cell lymphoma, one type of non-Hodgkin's lymphoma, and also has limited adverse effects (Non Patent Document 1). Rituximab alone, however, is low effective for some cancers. Although the combination therapy of rituximab with cyclophosphamide, doxorubicin, vincristine, and prednisolone has been adopted, the development of more effective therapeutic agents has been desired (Non Patent Documents 2 and 3). Accordingly, an antitumor antibody targeting a new antigen has been required. A monoclonal antibody against MHC class II is expected to have anti-malignant lymphoma activity as a clinical antibody recognizing an antigen different from that recognized by rituximab. Unfortunately, an anti-MHC class II antibody, for example, an antibody against HLA-DR, has previously been developed, but has not been used as a therapeutic agent (Patent Document 1).

CITATION LIST

Patent Document

Patent Document 1: WO2003/033538

Non Patent Document

Non Patent Document 1: McLaughlin P. et al., J Clin Oncol. (1998), 16, 2825-2833
Non Patent Document 2: Coiffier B. et al., New England Journal of Medicine (2002), 346, 235-242
[Non Patent Document 3] Cancer Support, 2005, October issue

SUMMARY OF THE INVENTION

Problems to be Solved by the Invention

An object of the present invention is to provide a novel therapeutic agent specific for a malignant tumor expressing MHC class II, particularly, malignant lymphoma.

Means for Solving the Problems

The present inventors have conducted various studies to develop a pharmaceutical agent specifically acting on a malignant tumor expressing MHC class II, particularly, malignant lymphoma. The present inventors have prepared fusion cells using the antibody-producing cells of a non-human animal immunized with two types of malignant lymphoma, not with one type of malignant lymphoma, and further selected, from among the fusion cells, a clone producing a monoclonal antibody which reacts with malignant lymphoma different from the two types and has cytotoxic activity against the malignant lymphoma. The obtained monoclonal antibody has been found to have cytotoxic activity against many types of malignant lymphoma with weak cytotoxic activity against the other cells and to be useful as a selective therapeutic agent for malignant lymphoma. Also, the present inventors have used malignant lymphoma extracts to find that the obtained monoclonal antibody is specifically bound to an HLA-DRβ chain, one of the molecules constituting MHC class II expressed on malignant lymphoma surface. The present inventors have further identified the sequences of the variable regions of the monoclonal antibody and determined an epitope to which the monoclonal antibody binds. On the basis of these findings, the present invention has been completed.

Specifically, the present invention provides the followings:
[1] An antibody recognizing a protein constituting MHC class II expressed on a malignant tumor, the antibody comprising at least one selected from light chain CDR1 (amino acid sequence represented by positions 49 to 54 of SEQ ID NO: 54), light chain CDR2 (amino acid sequence represented by positions 69 to 84 of SEQ ID NO: 54), light chain CDR3 (amino acid sequence represented by positions 117 to 128 of SEQ ID NO: 54), heavy chain CDR1 (amino acid sequence represented by positions 46 to 55 of SEQ ID NO: 56), heavy chain CDR2 (amino acid sequence represented by positions 71 to 77 of SEQ ID NO: 56), and heavy chain CDR3 (amino acid sequence represented by positions 100 to 108 of SEQ ID NO: 56).
[2] The antibody recognizing a protein constituting MHC class II expressed on a malignant tumor according to [1], wherein the antibody has the following light chain (a) or (b):
(a) a light chain having a light chain variable region comprising an amino acid sequence represented by positions 19 to 143 of SEQ ID NO: 54; or
(b) a light chain having a light chain variable region comprising an amino acid sequence wherein one or several amino acids are deleted, substituted, and/or added in the amino acid sequence represented by positions 19 to 143 of SEQ ID NO: 54.
[3] The antibody according to [1] or [2], wherein the antibody has the following heavy chain (c) or (d):
(c) a heavy chain having a heavy chain variable region comprising an amino acid sequence represented by positions 23 to 132 of SEQ ID NO: 56; or
(d) a heavy chain having a heavy chain variable region comprising an amino acid sequence wherein one or several amino acids are deleted, substituted, and/or added in the amino acid sequence represented by positions 23 to 132 of SEQ ID NO: 56.
[4] An antibody recognizing a protein constituting MHC class II expressed on a malignant tumor, the antibody having an antigen recognition site binding to an epitope comprising at least an amino acid sequence CRHNYGVGESFT (SEQ ID NO: 1).
[5] The antibody according to [4], wherein the antigen recognition site further recognizes at least one selected from an amino acid sequence RNQKGHSGLQPRGFLS (SEQ ID NO:28), an amino acid sequence FFNGTERVR- LLERHF (SEQ ID NO:8), and an amino acid sequence RHNYGAVESFTVQRR (SEQ ID NO: 15).

[6] The antibody according to any one of [1] to [5], wherein the antibody has specific cytotoxic activity against the malignant tumor.

[7] The antibody according to any one of [1] to [6], wherein the malignant tumor is malignant lymphoma.

[8] The antibody according to any one of [1] to [6], wherein the protein constituting MHC class II is at least one of HLA-DPβ, HLA-DQβ, and HLA-DRβ.

[9] The antibody according to [8], wherein the protein constituting MHC class II is HLA-DRβ.

[10] A pharmaceutical composition comprising an antibody according to any one of [1] to [9].

[11] A therapeutic agent for a malignant tumor expressing MHC class II, comprising an antibody according to any one of [1] to [9] as an active ingredient.

[12] A reagent for detecting a malignant tumor expressing MHC class II, comprising an antibody according to any one of [1] to [9].

[13] A method for treating a malignant tumor expressing MHC class II, comprising administering an effective amount of an antibody according to any one of [1] to [9].

[14] A method for preparing a monoclonal antibody having cytotoxic activity against malignant lymphoma cells, comprising the steps of: alternately immunizing a non-human animal with two types of malignant lymphoma cell lines at least twice or more per cell line; fusing an antibody-producing cell derived from the immunized non-human animal with a myeloma cell to prepare a hybridoma; and culturing the obtained hybridoma.

[15] The method for preparing a monoclonal antibody having cytotoxic activity against malignant lymphoma cells according to [14], wherein the monoclonal antibody produced from the hybridoma binds to a malignant lymphoma cell line different from the two types of malignant lymphoma cell lines.

[16] The method for preparing a monoclonal antibody having cytotoxic activity against malignant lymphoma cells according to [15], wherein the two types of malignant lymphoma cell lines used in immunization and the malignant lymphoma cell line different from the two types of malignant lymphoma cell lines have the same HLA.

[17] The method for preparing a monoclonal antibody having cytotoxic activity against malignant lymphoma cells according to any one of [14] to [16], wherein the two types of malignant lymphoma cell lines used in immunization are L428 and KMH-2.

[18] The method for preparing a monoclonal antibody having cytotoxic activity against malignant lymphoma cells according to [15] or [16], wherein the malignant lymphoma cell line different from the two types of malignant lymphoma cell lines is L540.

[19] A hybridoma deposited under deposition No. FERM BP-11418.

[20] An antibody produced by a hybridoma according to [19].

Effects of the Invention

The antibody of the present invention specifically recognizes MHC class II expressed on malignant lymphoma and has potent cytotoxic activity against the malignant lymphoma. Thus, the antibody of the present invention is useful as a selective therapeutic agent for a malignant tumor expressing MHC class II, particularly, malignant lymphoma.

Moreover, an antibody recognizing a malignant lymphoma-specific antigen can be prepared efficiently using the method of the present invention.

BRIEF DESCRIPTION OF THE DRAWINGS

FIG. 15 shows a gene (SEQ ID NO:55)encoding the heavy chain variable region (SEQ ID NO:56)of the monoclonal antibody of the present invention.

FIG. 16 shows a gene (SEQ ID NO:53)encoding the light chain variable region (SEQ ID NO:54) of the monoclonal antibody of the present invention.

MODES FOR CARRYING OUT THE INVENTION

Figure 1:
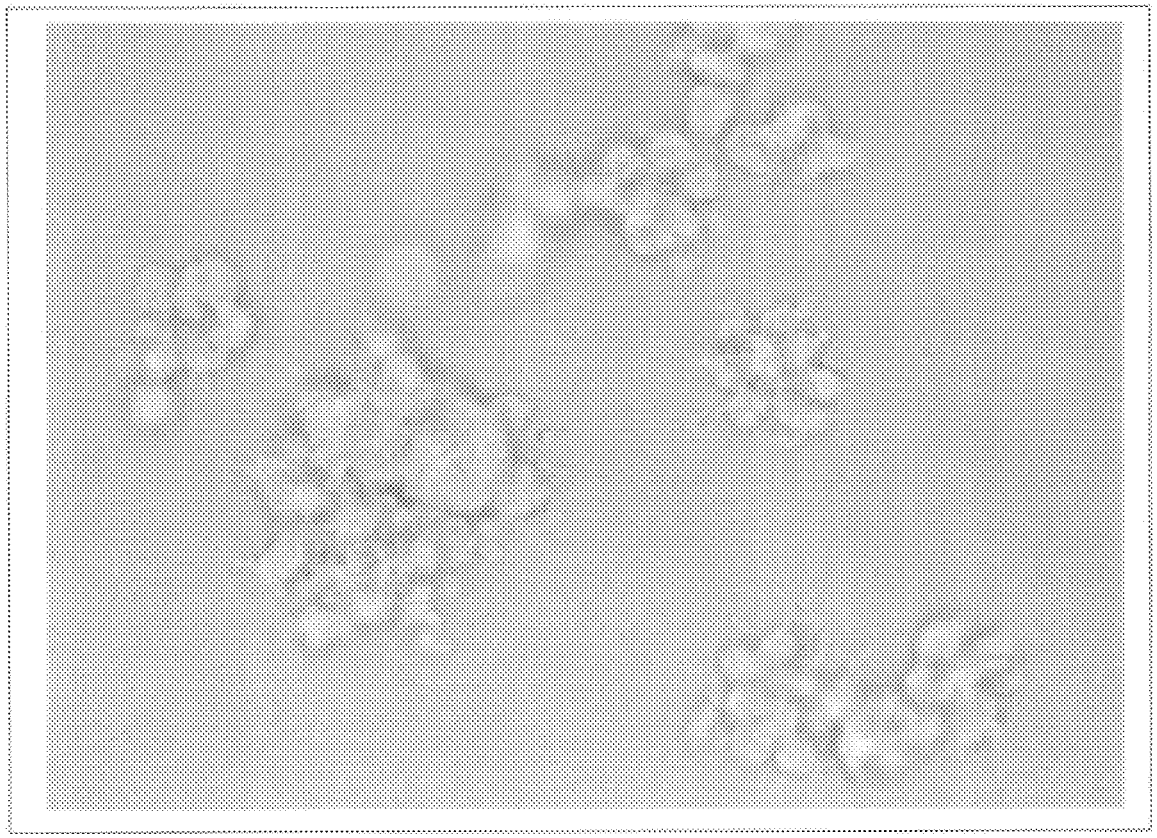
FIG. 1 is a diagram showing the effects of the monoclonal antibody of the present invention on malignant lymphoma (5 minutes later).

In the present specification, amino acids, peptides, and proteins are indicated by abbreviations adopted by the IUPAC-IUB Commission on Biochemical Nomenclature (CBN), as shown below. Also, the sequence of amino acid residues of each peptide or protein is described from the N terminus on the left to the C terminus on the right, unless otherwise specified.
Ala or A: alanine
Val or V: valine
Leu or L: leucine
Ile or I: isoleucine
Pro or P: proline
Phe or F: phenylalanine
Trp or W: tryptophan
Met or M: methionine
Gly or G: glycine
Ser or S: serine
Thr or T: threonine
Cys or C: cysteine
Gln or Q: glutamine
Asn or N: asparagine
Tyr or Y: tyrosine
Lys or K: lysine
Arg or R: arginine
His or H: histidine
Asp or D: aspartic acid
Glu or E: glutamic acid The present invention provides an antibody which specifically recognizes MHC class II expressed on malignant lymphoma and has potent cytotoxic activity against the malignant lymphoma. The present invention also provides a method for efficiently preparing an antibody recognizing a malignant lymphoma-specific antigen.

Anti-MHC Class II Antibody

The major histocompatibility complex (MHC) is a transmembrane glycoprotein molecule found on cell surface and plays a role in presenting various protein fragments (peptides) from within the cell onto its surface. The MHC molecules are classified into two classes: class I and class II. MHC class I presents an endogenous antigen from within the cell, while MHC class II binds to and presents peptides resulting from the endocytic uptake and subsequent degradation of an exogenous antigen. Of these molecules, MHC class II is expressed on, for example, antigen-presenting cells such as macrophages, dendritic cells, activated T cells, and B cells. The human MHC class II includes three types: HLA-DR, HLA-DQ, and HLA-DP. These molecules each function as a heterodimer of two protein subunits of α and β chains.

The antibody of the present invention is not particularly limited as long as the antibody recognizes a protein constituting MHC class II expressed on a malignant tumor and has cytotoxic activity against the malignant tumor. The antibody of the present invention may be a monoclonal antibody or a polyclonal antibody. The antibody of the present invention also includes, but not limited to: natural antibodies; chimeric antibodies, humanized antibodies, and single-chain antibodies which can be produced using gene recombination techniques; human antibodies which can be produced using human antibody-producing transgenic animals or the like; antibody fragments prepared with Fab expression libraries; and fragments thereof having antigen binding affinity.

The antibody of the present invention has the ability to bind to at least a sequence CRHNYGVGESFT (SEQ ID NO: 1) in HLA-DR52 and is considered to recognize this region.

In addition, the antibody of the present invention has the ability to bind to at least one selected from an amino acid sequence RNQKGHSGLQPRGFLS (SEQ ID NO: 28), an amino acid sequence FFNGTERVRLLERHF (SEQ ID NO: 8), and an amino acid sequence RHNYGAVESFTVQRR (SEQ ID NO: 15).

Alternatively, the antibody of the present invention is not particularly limited as long as the antibody recognizes HLA-DR, HLA-DP, or HLA-DQ expressed on a malignant tumor and has cytotoxic activity against the malignant tumor. The antibody of the present invention may be, for example, a monoclonal antibody recognizing HLA-DR expressed on malignant lymphoma, the monoclonal antibody comprising at least one complementarity determining region (CDR) selected from light chain CDR1 (amino acid sequence represented by positions 49 to 54 of SEQ ID NO: 54), light chain CDR2 (amino acid sequence represented by positions 69 to 84 of SEQ ID NO: 54), light chain CDR3 (amino acid sequence represented by positions 117 to 128 of SEQ ID NO: 54), heavy chain CDR1 (amino acid sequence represented by positions 46 to 55 of SEQ ID NO: 56), heavy chain CDR2 (amino acid sequence represented by positions 71 to 77 of SEQ ID NO: 56), and heavy chain CDR3 (amino acid sequence represented by positions 100 to 108 of SEQ ID NO: 56). Also, the antibody of the present invention may be an antibody recognizing MHC class II expressed on a malignant tumor and having cytotoxic activity against the malignant tumor, the antibody comprising a light chain variable region comprising an amino acid sequence represented by positions 19 to 143 of SEQ ID NO: 54 and/or a heavy chain variable region comprising an amino acid sequence represented by positions 23 to 132 of SEQ ID NO: 56. In this context, the cytotoxic activity includes complement-dependent cytotoxicity (CDC) and antibody-dependent cell-mediated cytotoxicity (ADCC).

Alternatively, the antibody of the present invention may be an antibody recognizing MHC class II expressed on a malignant tumor, the antibody comprising a light chain variable region comprising an amino acid sequence represented by positions 19 to 143 of SEQ ID NO: 54 and/or a heavy chain variable region comprising an amino acid sequence represented by positions 23 to 132 of SEQ ID NO: 56, or the antibody comprising a heavy chain variable region comprising an amino acid sequence wherein one or several amino acids are deleted, substituted, and/or added in the defined amino acid sequence and/or a light chain variable region comprising an amino acid sequence wherein one or several amino acids are deleted, substituted, and/or added in the defined amino acid sequence, as long as the antibody recognizes MHC class II expressed on a malignant tumor and has cytotoxic activity against the malignant tumor. In this context, the "amino acid sequence wherein one or several amino acids are deleted, substituted, and/or added in the defined amino acid sequence" means an amino acid sequence modified by a well known method such as site-directed mutagenesis or by the naturally occurring substitution or the like of one or several amino acids. The number of modified amino acids is preferably 1 to 50, more preferably 1 to 30, even more preferably 1 to 10, even more preferably 1 to 5, even more preferably 1 or 2. Alternatively, the antibody of the present invention may be an antibody having cytotoxic activity against a malignant tumor, the antibody comprising a heavy chain variable region or a light chain variable region comprising an amino acid sequence having at least 70%, preferably 80%, more preferably 90%, particularly preferably 95% sequence identity to the defined amino acid sequence.

Furthermore, the antibody of the present invention may be a humanized antibody comprising the heavy and light chain variable regions of a non-human mammal antibody, for example, a mouse antibody, and the heavy and light chain constant regions of a human antibody. Such an antibody can be obtained by: linking a mouse antibody variable region-encoding DNA to a human antibody constant region-encoding DNA; incorporating the resulting product into an expression vector; and transforming a host with the expression vector to produce the antibody of interest. This humanized antibody, also called a reshaped human antibody, contains non-human mammal (e.g., mouse) antibody CDRs grafted into human antibody CDRs. This grafting can be performed by a generally known gene recombination approach. Specifically, a DNA sequence encoding mouse antibody CDRs linked to human antibody framework regions (FRs) is designed and then synthesized by PCR using several oligonucleotides prepared to have terminal overlapping sites. The obtained DNA is linked to a human antibody constant region-encoding DNA and subsequently incorporated into an expression vector. A host is transformed with this expression vector to produce the antibody of interest (see European Patent Application Publication No. EP239400 and International Publication No. WO96/02576). The human antibody FRs to be linked via CDRs are selected such that the complementarity determining regions form favorable antigen-binding sites. If necessary, amino acid(s) in the framework regions of the antibody variable region may be substituted such that the complementarity determining regions of the reshaped human antibody form appropriate antigen-binding sites (Sato, K. et al., Cancer Res, 1993, 53, 851-856).

In addition, the human antibody can also be obtained by a known method. For example, human lymphocytes are sensitized in vitro with the desired antigen or cells expressing the desired antigen. The sensitized lymphocytes are fused with human myeloma cells, for example, U266. The desired human antibody having binding activity against the antigen can be obtained from the fusion cells (see JP-B-1-59878). Alternatively, the desired human antibody may be obtained by immunizing transgenic animals having all repertoires of human antibody genes with the desired antigen (see WO93/12227, WO92/03918, WO94/02602, WO94/25585, WO96/34096, and WO96/33735). In addition, the panning technique of obtaining human antibodies using human antibody libraries is also known. For example, human antibody variable regions are expressed as single-chain antibodies (scFvs) on phage surface by a phage display method. As a result, a phage binding to the antigen can be selected. The gene of the selected phage can be analyzed to determine a DNA sequence encoding the variable region of the human antibody binding to the antigen. On the basis of the determined DNA sequence of scFv binding to the antigen, an appropriate expression vector containing the sequence can be prepared to obtain the human antibody of interest. These methods have already been well known and can be performed with reference to WO92/01047, WO92/20791, WO93/06213, WO93/11236, WO93/19172, WO95/01438, and WO95/15388.

The class of the antibody is not particularly limited. The antibody of the present invention encompasses antibodies having any isotype such as IgG, IgM, IgA, IgD, or IgE. In consideration of easy purification, etc., IgG is preferred, with IgG1a more preferred.

Examples of functional fragments include small antibodies such as antibody fragments, and modified antibodies. Specific examples of the antibody fragments include Fab, Fab', F(ab')2, Fv, and Diabody. Such antibody fragments may be obtained by constructing genes encoding these antibody fragments, introducing the genes into expression vectors, and then allowing the genes to be expressed in appropriate host cells (see e.g., Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; and Bird, R. E. and Walker, B. W., Trends Biotechnol. (1991) 9, 132-137).

Pharmaceutical Composition

The pharmaceutical composition, such as a therapeutic agent for a malignant tumor expressing MHC class II, of the present invention can be formulated, for example, by mixing, dissolving, emulsifying, encapsulating, or freeze-drying the antibody of the present invention, together with a pharmaceutically acceptable carrier well known in the technical field.

A disease to be treated is not particularly limited as long as the disease is a malignant tumor expressing MHC class II. Examples thereof include malignant lymphoma. Examples of the malignant lymphoma include, but not limited to, leukemia (including chronic lymphocytic leukemia and acute lymphocytic leukemia) and lymphoma (including non-Hodgkin's lymphoma, Hodgkin's lymphoma, T cell lymphoma, B cell lymphoma, Burkitt lymphoma, malignant lymphoma, diffuse lymphoma, and follicular lymphoma). The tumor to which the antibody of the present invention is applied is not limited to one type and may be plural types of tumors occurring in combination.

Preferable preparations for oral administration are, for example, liquid formulations comprising an effective amount of the antibody of the present invention dissolved in a diluent such as water or saline; capsules, granules, powders, or tablets comprising an effective amount of the antibody of the present invention in a solid or granule form; suspensions comprising an effective amount of the antibody of the present invention suspended in an appropriate dispersion medium; and emulsions comprising a dispersed and emulsified solution containing an effective amount of the antibody of the present invention in an appropriate dispersion medium.

For parenteral administration, the antibody of the present invention can be prepared, together with a pharmaceutically acceptable solvent, excipient, binder, stabilizer, dispersant, and the like, into dosage forms such as injectable solutions, suspensions, emulsions, creams, ointments, inhalants, or suppositories. For formulation for injection, the antibody of the present invention can be dissolved in a physiologically compatible buffer solution such as an aqueous solution, preferably, a Hank's solution, a Ringer's solution, or a physiological saline buffer solution. In addition, the pharmaceutical agent of the present invention can assume a form such as a suspension, a solution, or an emulsion in an oily or aqueous vehicle. Alternatively, the antibody of the present invention may be produced in a powder form and prepared, before use, into an aqueous solution or a suspension using sterilized water or the like. For administration by inhalation, the antibody of the present invention can be pulverized and prepared as a powder mixture with an appropriate base such as lactose or starch. In order to produce suppository formulation, the antibody of the present invention can be mixed with a common suppository base such as cacao butter. The therapeutic agent of the present invention may be further encapsulated in a polymer matrix or the like and formulated as a sustained-release preparation.

Alternatively, the antibody of the present invention may be conjugated with, for example, a radionuclide such as iodine, yttrium, indium, or technetium [J. W. Goding, Monoclonal Antibodies: principles and practice., 1993 Academic Press], a bacterial toxin such as pseudomonas toxin, diphtheria toxin, or ricin, a chemotherapeutic such as methotrexate, mitomycin, or calicheamicin [D. J. King, Applications and Engineering of Monoclonal Antibodies., 1998 T. J. International Ltd.; and M. L. Grossbard., Monoclonal Antibody-Based Therapy of Cancer., 1998 Marcel Dekker Inc.], or a prodrug such as maytansinoid [Chari et al., Cancer Res., 1992 Vol. 52: 127;

and Liu et al., Proc. Natl. Acad. Sci. USA, 1996 Vol. 93: 8681] to thereby further potentiate its therapeutic effects on malignant lymphoma.

The dose of the antibody of the present invention differs depending on the symptoms of a patient, an administration route, a body weight, age, etc., and is preferably, for example, 1 µg to 500 mg per day in adult.

Treatment Method

Malignant lymphoma treatable by a biologically active substance can be treated using the pharmaceutical composition of the present invention. Thus, the present invention provides a method for treating malignant lymphoma, comprising administering an effective amount of the antibody of the present invention to a subject in need thereof.

Reagent for Detecting Malignant Tumor Expressing MHC Class II

The present invention provides a reagent for detecting the presence of a malignant tumor expressing MHC class II, the reagent comprising the antibody of the present invention. The antibody of the present invention may be labeled. This detection reagent detects the presence of a malignant tumor expressing MHC class II by detecting antigen-antibody reaction. Thus, the detection reagent of the present invention may further comprise, if desired, various reagents for carrying out antigen-antibody reaction, for example, a secondary antibody, a coloring reagent, a buffer solution, an instruction, and/or an instrument, for use in ELISA, etc.

Method for Preparing Antibody Specifically Recognizing Malignant Lymphoma

The monoclonal antibody of the present invention can be prepared by a method comprising the steps of: alternately immunizing a non-human animal with two types of malignant lymphoma cell lines twice or more per cell line; fusing an antibody-producing cell derived from the immunized non-human animal with a myeloma cell to prepare a hybridoma; and culturing the obtained hybridoma.

The two types of malignant lymphoma cell lines used in immunization (hereinafter, also referred to as immunizing cell lines) can be two cell lines selected from among known established malignant lymphoma cell lines and may be Hodgkin's lymphoma cell lines or non-Hodgkin's lymphoma cell lines. Examples thereof include two cell lines selected from KMH-2, L428, L540, RAJI, Daudi, KARPAS-299, C1R, and HT. Preferably, two cell lines having the same HLA are selected from them. For example, KMH-2, L428, and L540 all have HLA-A3. Thus, two types are preferably selected from these cell lines and used. Particularly preferably, KMH-2 and L428 are used.

Each non-human animal is alternately immunized with these two types of immunizing cell lines twice or more per cell line. Specifically, the non-human animal is alternately immunized with these two types of immunizing cell lines twice or more per cell line, i.e., a total of four times or more. The number of immunization is more preferably 2 to 5 per cell line, even more preferably 3 or more per cell line, particularly preferably 3 times per cell line. The single dose of each immunizing cell line used in immunization is $2 \times 10^7$ to $10^8$ cells, particularly preferably $3 \times 10^7$ cells.

Examples of immunization means include subcutaneous injection, intraperitoneal injection, intravenous injection, intradermal injection, intramuscular injection, and injection into footpads. Intraperitoneal injection is preferred. The interval between immunizations is preferably, for example, 2 weeks to 4 weeks. Then, an antibody titer against the antigen is determined in the sera of the immunized animals. An animal confirmed to have a sufficiently high antibody titer is used as a source of antibody-producing cells. Antibody-producing cells derived from the animal 3 to 5 days after the final immunization are preferably used.

Examples of the non-human animal used in immunization include mice, rats, guinea pigs, hamsters, rabbits, and pigs. Mice are particularly preferred. Examples of the antibody-producing cell include spleen, lymph node, and bone marrow cells. Spleen cells are preferred.

Examples of the myeloma cell used in cell fusion include cells derived from animals such as mice, rats, guinea pigs, hamsters, and rabbits. A mouse-derived established myeloma cell line is preferred. Specific examples thereof include P3×63Ag8U.1 (P3-U1), P3/NSI/1-Ag4-1 (NS-1), Sp2/o-Ag14 (SP-2), P3×63Ag8.653 (653), and P3×63Ag8 (×63).

The cell fusion between the antibody-producing cells and the myeloma cells is performed, for example, by mixing the antibody-producing cells and the myeloma cells at a ratio of 0.5:1 to 2:1 in terms of the number of cells and adding 50 w/v % polyethylene glycol (molecular weight: 1000 to 4000) to the cell mixture. Then, fusion cells are selected by screening using a HAT medium.

A hybridoma which reacts with a malignant lymphoma cell line (hereinafter, also referred to as a selection cell line) different from the two types of immunizing cell lines and produces a monoclonal antibody having cytotoxic activity against the malignant lymphoma cell line is selected from the obtained hybridomas. The selection cell line can be any cell line different from the two types of immunizing cell lines and can be selected from the malignant lymphoma cell lines mentioned above. The selection cell line may be a Hodgkin's lymphoma cell line or a non-Hodgkin's lymphoma cell line. The selection cell line is more preferably a cell line having the same HLA as the cell lines for immunization and is more preferably a cell line having HLA-A3. Particularly, L540 is preferred.

The hybridoma of the present invention is selected, for example, by adding the supernatants of the hybridomas to be tested to the culture solution of the selection cell line and selecting a clone producing a monoclonal antibody toxic to the selection cell line by a dye exclusion test using a dye such as trypan blue.

Examples of the hybridoma of the present invention thus obtained include 4713 mAb (FERM BP-11418). 4713 mAb was deposited on Sep. 28, 2010 with International Patent Organism Depositary, National Institute of Advanced Industrial Science and Technology (Tsukuba Central 6, 1-1-1 Higashi, Tsukuba, Ibaraki 305-8566 Japan).

The hybridoma of the present invention can be cultured to thereby obtain a monoclonal antibody useful as a therapeutic agent for malignant lymphoma. Large-scale culture is performed by rotational or spinner culture using large-scale culture vessels or by culture using a hollow fiber system. A supernatant from this large-scale culture can be purified by a method well known by those skilled in the art, such as gel filtration, to obtain the monoclonal antibody of the present invention. Alternatively, the hybridoma may be grown in the peritoneal cavity of a mouse of the same line to thereby obtain an ascitic fluid containing the monoclonal antibody of the present invention in large amounts. Also, the obtained monoclonal antibody can be prepared into a chimeric antibody or a humanized antibody by the methods mentioned above.

EXAMPLES

Example 1

(1) Immunization Method

An eight-week-old female BALB/c mouse was alternately immunized with two types of Hodgkin's lymphoma cell lines ($3 \times 10^7$ cells each) three times per cell line (a total of six times) at 2-week intervals. Cultured cells of each cell line were washed twice with saline, then resuspended in 200 μL of saline, and intraperitoneally injected to the mouse without use of adjuvants.

These two types of Hodgkin's lymphoma cell lines were L428 and KM-H2 selected on the ground that they expressed HLA-A3.

(2) Cell Fusion 3 days after the final immunization, $10^8$ spleen cells of the immunized mouse were fused with $10^8$ P3U1 myeloma cells using PEG4000. This cell mixture was seeded in fifty 96-well flat-bottomed plates.

(3) Screening Method

HLA-A3-expressing Hodgkin's lymphoma L540 cells were added at a concentration of $2 \times 10^6$ cells/mL, together with 50 μL, of RPMI (containing 2% FCS), to a Fisher tube or another 96-well flat-bottomed plate, to which 50 μL of the cell culture supernatant from a positive well was then added, followed by incubation at 37° C. for 1 hour.

Trypan blue was added thereto to examine a clone producing an antibody killing the target L540 cells by a dye exclusion test (according to J. Exp. Med. Vol. 181 June 1995 p. 2008).

A hybridoma culture supernatant obtained by two limiting dilutions of the clone (designated as 4713 mAb) thus obtained or an ascitic fluid produced by a nude mouse was used in the subsequent experiments.

The subclass of the antibody was mouse IgG1.

Example 2

(Method)

The monoclonal antibody (4713 mAb) of the present invention was examined for its cytotoxic activity against the Hodgkin's lymphoma cells L428 and KM-H2 used in mouse immunization in the same way as in the examination of cytotoxic activity against L540. 4713 mAb was added at a concentration of 3 μg/mL to $2 \times 10^6$ cells/mL of L428 cells or KM-H2 cells. Change in the morphology of the cells was microscopically observed. The lethality of the KM-H2 cells was only 10% or less by 1-hour incubation. However, cell aggregation, which is often observed at a stage prior to cell death, was observed. Thus, cytotoxic activity brought about by 12-hour incubation was further examined in the same way as above.

(Results)

The results are shown in FIGS. 1 to 4.

Figure 2:
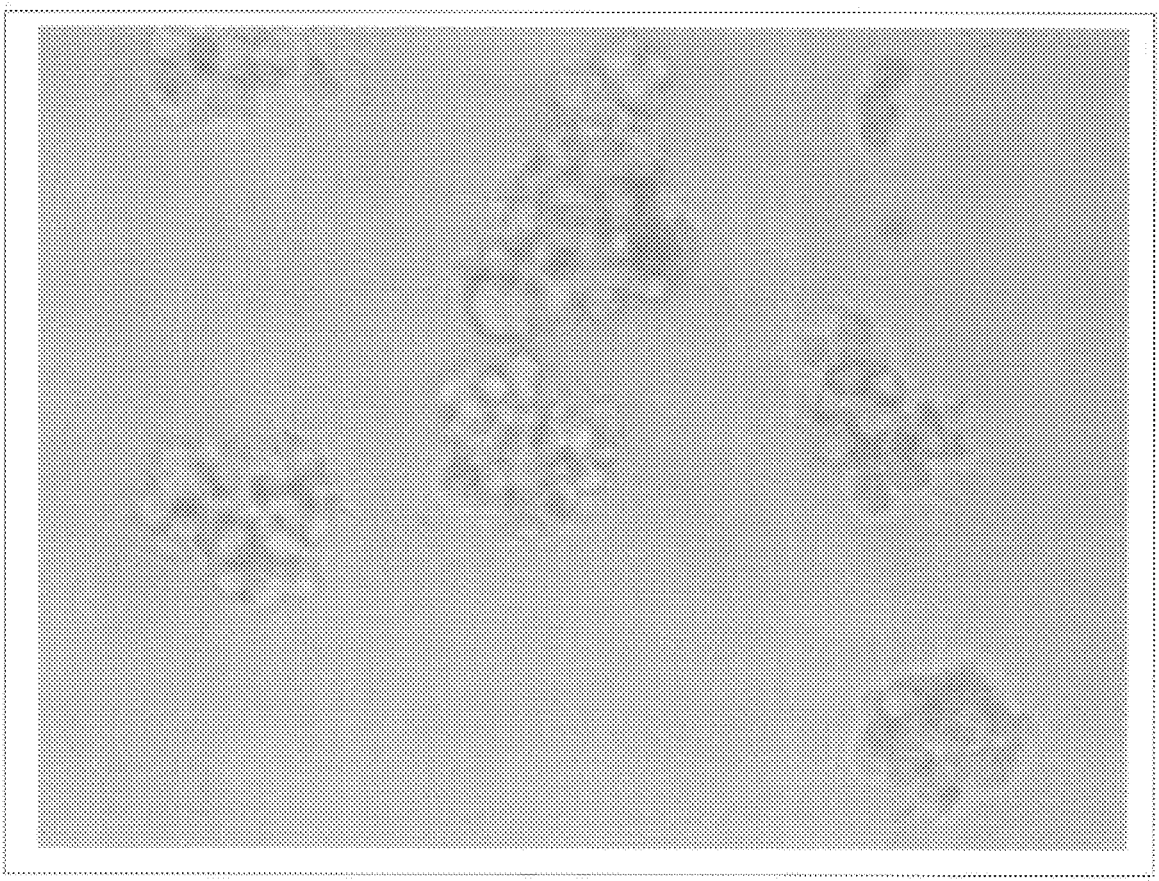
FIG. 2 is a diagram showing the effects of the monoclonal antibody of the present invention on malignant lymphoma (15 minutes later).
Figure 3:
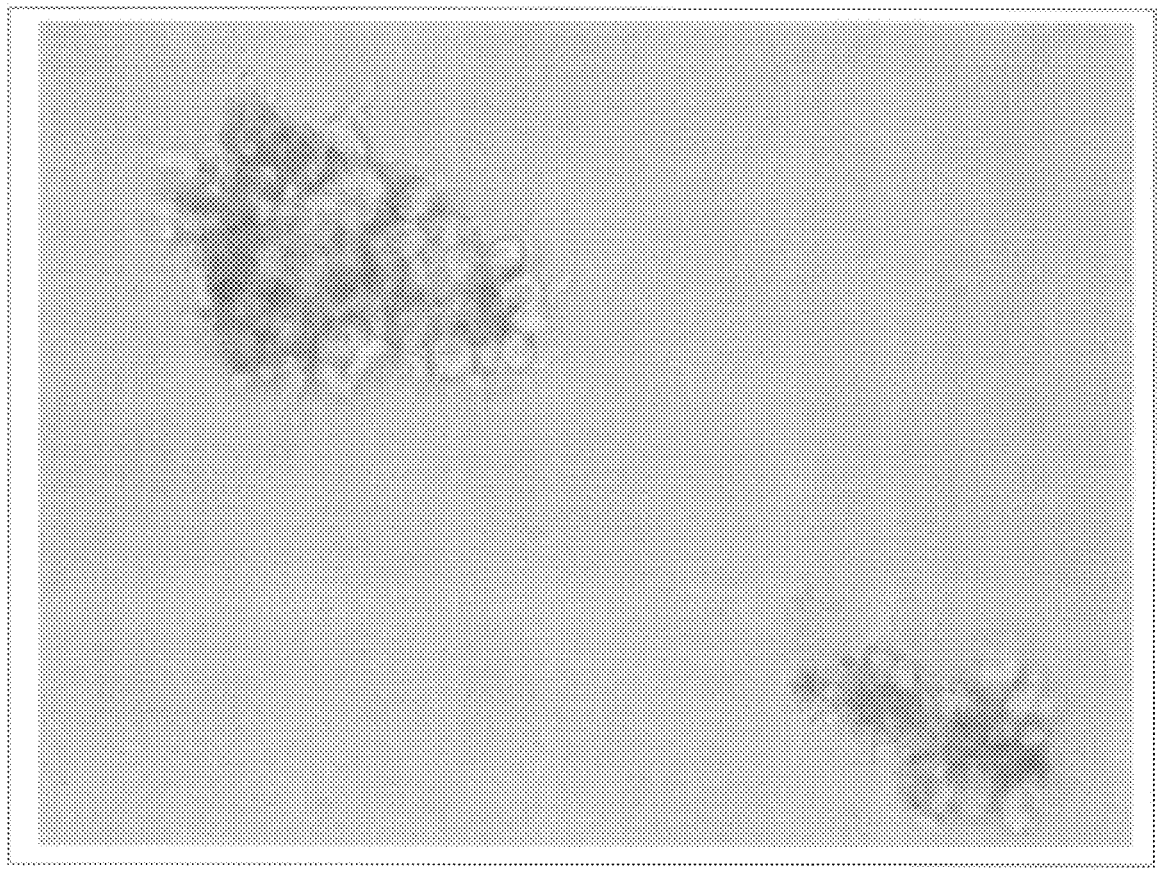
FIG. 3 is a diagram showing the effects of the monoclonal antibody of the present invention on malignant lymphoma (30 minutes later).
Figure 4:
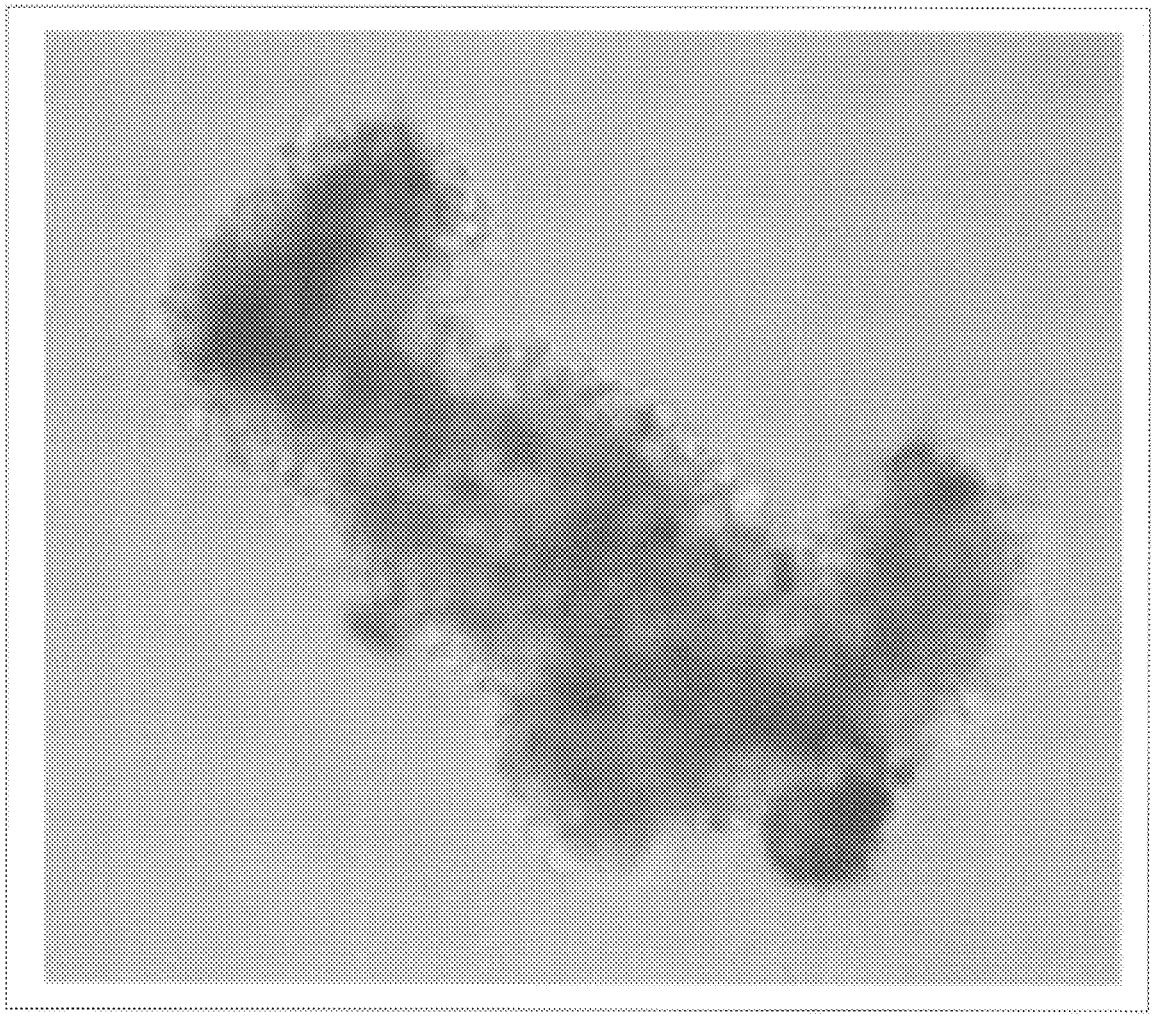
FIG. 4 is a diagram showing the effects of the monoclonal antibody of the present invention on malignant lymphoma (60 minutes later).

As is evident from FIGS. 1 to 4, the cells aggregated in several minutes (FIG. 1). On 15 minutes, some cells in the cell aggregates were stained blue by the addition of trypan blue, showing that cells killed by the antibody started to appear (FIG. 2). The incubation with the antibody for a time exceeding 30 minutes was confirmed to kill more than 30% cells (FIG. 3). The incubation with the antibody for 60 minutes lysed most of the cells through cell death. Remaining aggregates composed mainly of dead cells may also be observed (FIG. 4).

Example 3

Figure 5:
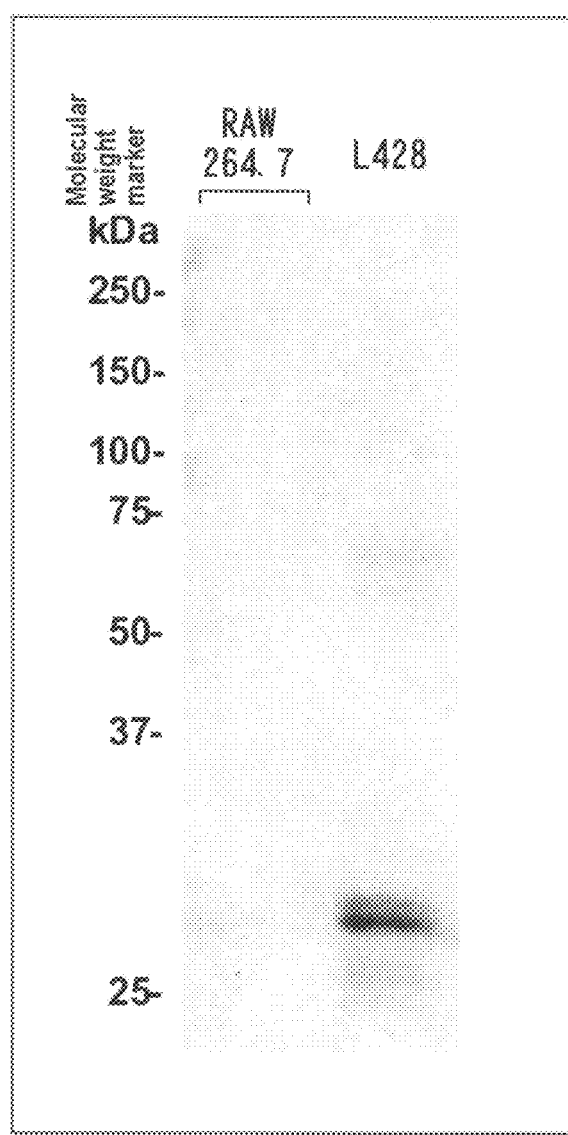
FIG. 5 shows Western blot results of the monoclonal antibody of the present invention.

Western blot results of the monoclonal antibody (4713 mAb) of the present invention are shown in FIG. 5.

Example 4

4713 mAb was examined for its cytotoxic activity against Burkitt lymphoma cells as lymphoma cells other than Hodgkin's lymphoma cells in the same way as in the Examples above. As a result, slightly more than 50% Burkitt lymphoma cells examined in the same way as the Hodgkin's lymphoma cells were also killed in 1 hour.

Example 5

4713 mAb was also examined for its cytotoxic activity against the other lymphoma cells in the same way as above. The results are shown in Table 1.

TABLE 1

| Cell line | cell type | cytotoxicity | comment |
|---|---|---|---|
| L428 | Hodgkin lymphoma | 92%/h | CD20(+)HLA-DR(+) |
| L540 | Hodgkin lymphoma | 40%/h | CD15(+)CD25(+) |
| KM-H2 | Hodgkin lymphoma | 32%/12 h | HLA-DR(+) |
| RAJI | Burkitt lymphoma | 51%/h | CD25(+)HLA-DR(+) |
| Daudi | Burkitt lymphoma | 56%/h | MHC class I defect |
| KARPAS-299 | T cell lymphoma | 34%/12 h | CD3(−)CD4(+) |
| C1R | B cell lymphoma | 65%/h | MHC class I defect |
| HT | B lymphoblast | 68%/h | diffuse mixed lymphoma |
| Normal human peripheral lymphocyte | | 0% | |

As is evident from Table 1, 4713 mAb is toxic to many types of malignant lymphoma cells, but not toxic to normal lymphocytes.

Example 6

The antibody of the present invention was analyzed for its ability to stain each lymphoma cell to which the antibody was confirmed to be cytotoxic and for the cytotoxicity sensitivity of the cell by flow cytometry.

Figure 6:
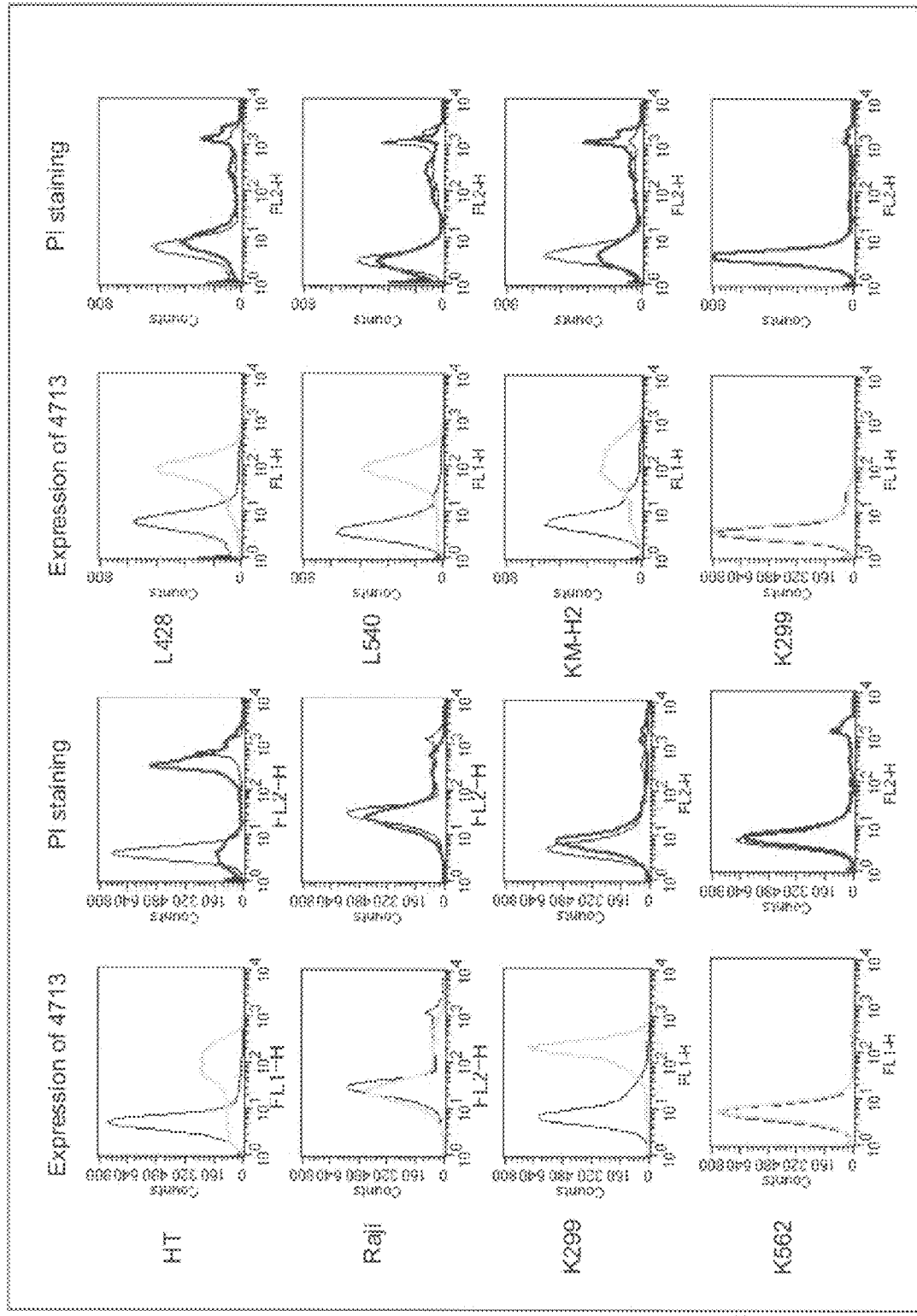
FIG. 6 shows results of analyzing the ability of the antibody of the present invention to stain each lymphoma cell (expression level of a cell surface antigen recognized by the antibody of the present invention) to which the antibody of the present invention was confirmed to be cytotoxic, and the cytotoxicity sensitivity of the cell by flow cytometry.
Figure 7:
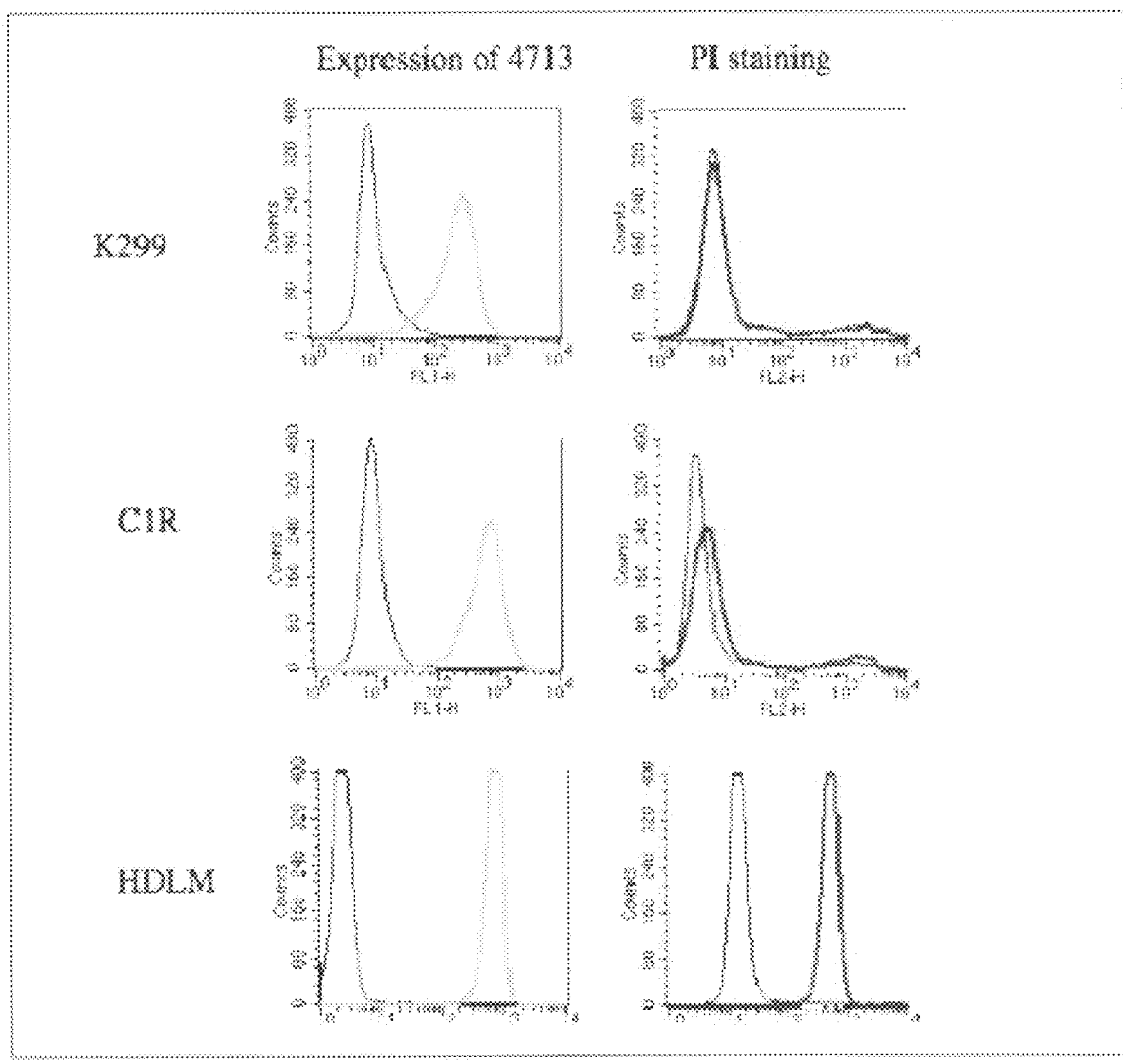
FIG. 7 shows results of analyzing the ability of the antibody of the present invention to stain each lymphoma cell (expression level of a cell surface antigen recognized by the antibody of the present invention) to which the antibody of the present invention was confirmed to be cytotoxic, and the cytotoxicity sensitivity of the cell by flow cytometry.

The antibody of the present invention was added to a cell suspension. 30 minutes later, the cells were washed and then reacted with fluorescein isothiocyanate (FITC)-conjugated rat anti-mouse immunoglobulin as a secondary antibody. The ability to stain the cells is shown in a histogram with a green line (FIGS. 6 and 7). Cells other than a chronic myelocytic leukemia-derived cell line K562 showed a great shift to the right of a base line indicated by black solid line, demonstrating that the cells were well stained. This means that the antibody recognized lymphoma cell surface. Also, the staining of these cells with propidium iodide (PI), which is incorporated only into dead cells, is shown in a histogram with a red line.

As is evident from the histograms, the incubation for mere 30 minutes already killed a considerable number of cells. Even cells, such as K562, showing a small shift of the green line, i.e., having a small number of surface antigens (the antibody is hardly bound to such cells), were confirmed to be dead, although the dead cells were few in number.

Example 7

Peripheral blood was collected from a healthy person. Red blood cells were removed by lysis with tris-buffered ammonium chloride. Then, the resulting blood was incubated, either directly or after 24-hour stimulation with Con A, with the antibody of the present invention for 1 hour. After subsequent staining with an FITC-labeled anti-mouse immunoglobulin antibody as a secondary antibody, the blood was analyzed by flow cytometry. In this test, the number of dead cells was also analyzed by the addition of PI.

(Results)

Figure 8:
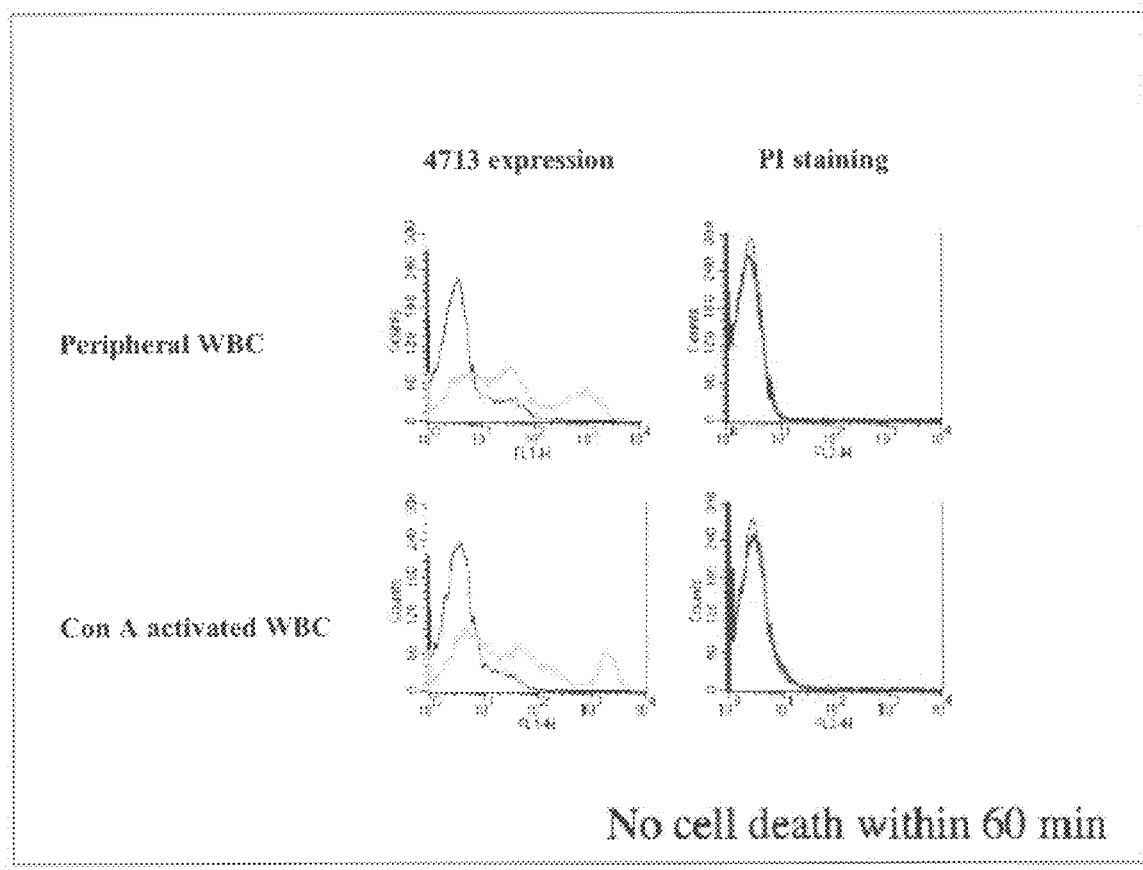
FIG. 8 shows results of analyzing the effects of the antibody of the present invention on human peripheral blood by flow cytometry.

As shown in FIG. 8, the monoclonal antibody of the present invention partially stained the peripheral blood of the healthy person, but did not kill the peripheral blood cells of the healthy person for at least 60 minutes. The same results were obtained from the case of 24-hour activation with concanavalin A (Con A).

Example 8

Reactivity of Antibody of Present Invention with TRAIL death receptors DR4 and DR5

(Method)

Hamster-derived BHK cells transfected with the DR4 receptor or DR5 receptor gene were incubated with the antibody of the present invention for 1 hour and analyzed by flow cytometry in the same way as in Example 6.

(Results)

Figure 9:
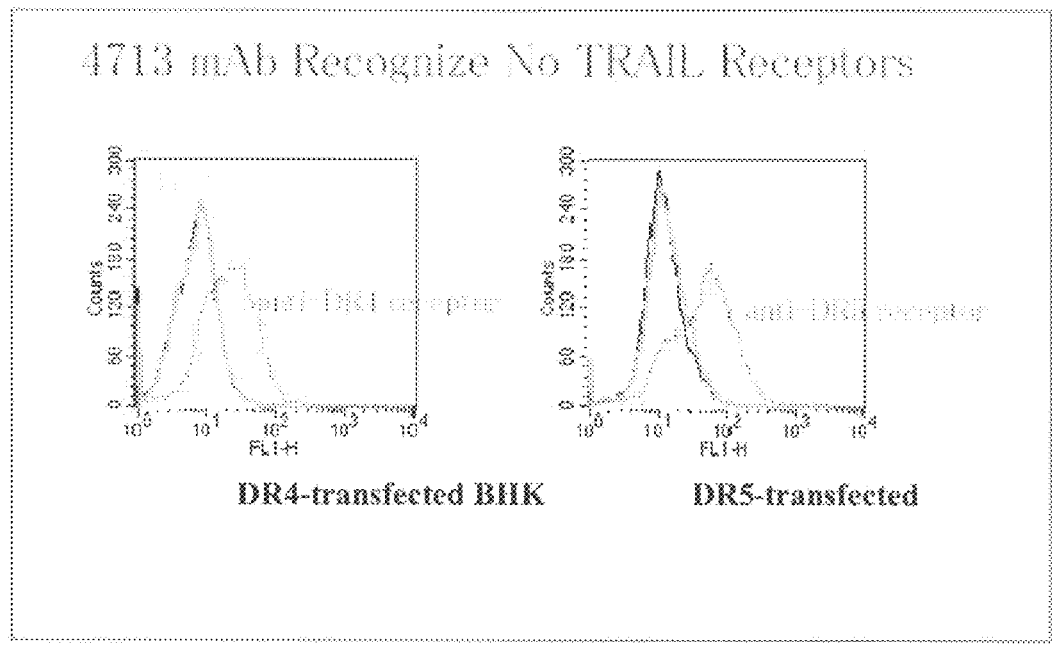
FIG. 9 shows the reactivity of the antibody of the present invention with TRAIL death receptors DR4 and DR5.

In order to confirm whether the antibody of the present invention targets a TNF-related apoptosis inducing ligand (TRAIL) death receptor DR4 or DR5 known as a death receptor (cell death-inducing antigen), the antibody of the present invention was examined for its ability to stain hamster-derived BHK cells transfected with the DR4 receptor or DR5 receptor gene in the same way as above. As a result, the cells were stained by a known antibody against DR4 receptor or DR5 receptor (red line), but not stained by the antibody of the present invention (FIG. 9). These results demonstrated that the present antibody does not target a TRAIL death receptor such as DR4 or DR5.

Example 9

Binding of 4713 mAb with Malignant Lymphoma Cell Line

Figure 10:
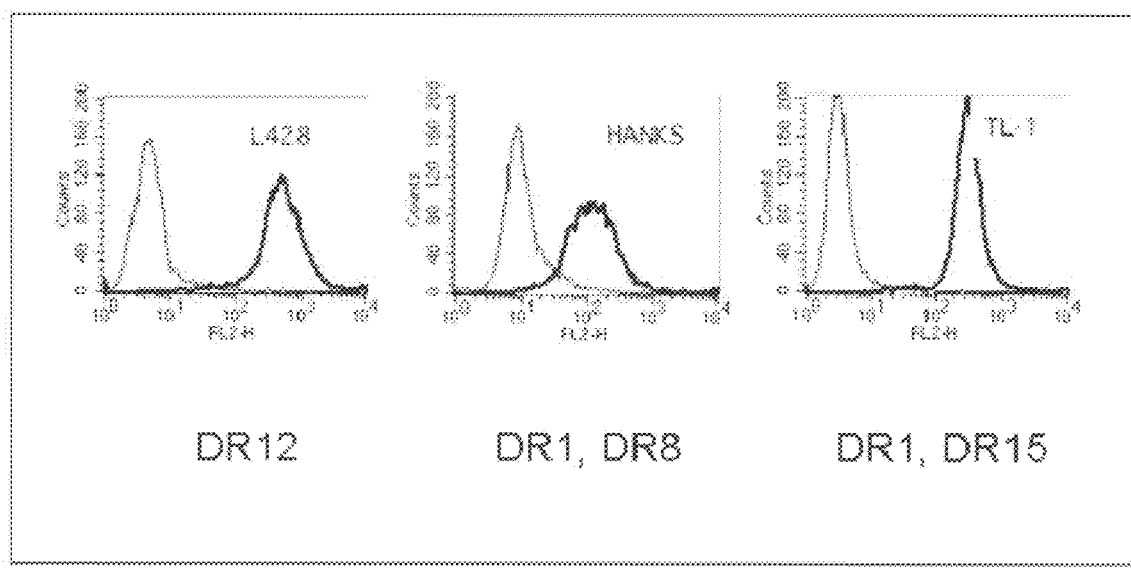
FIG. 10 shows results of analyzing the binding affinity of the monoclonal antibody of the present invention for L428, HANKS, and TL-1 by flow cytometry.

L428, HANK1, and TL1 cells were analyzed using a flow cytometer to confirm the binding of 4713 mAb thereto (FIG. 10).

Example 10

Identification of Target Antigen of 4713 mAb

According to the protocol of GE Healthcare Japan Corp., 4713 mAb (5 mg) was conjugated to HiTrap NHS-Activated HP (capacity: 1 mL, GE Healthcare #17-0716-01) to prepare a 4713 mAb column. L428, HANKS, or TL cells ($1 \times 10^8$ cells) were suspended in a phosphate buffer solution containing 1% Nonidet P-40 (Wako Pure Chemical Industries, Ltd.) and a protease inhibitor (Roche Diagnostics K.K.). Each cell suspension was incubated at 4° C. for 5 minutes and then centrifuged in a tabletop centrifuge (1500 rpm, 5 min.). A supernatant fraction was recovered and applied to the 4713 mAb column equilibrated with a phosphate buffer solution. After washing with a phosphate buffer solution, fractions were eluted with a 0.1% aqueous glycine-HCl solution (pH 2.7) and neutralized with a 1 M aqueous tris-HCl solution (pH9.0).

Figure 11:
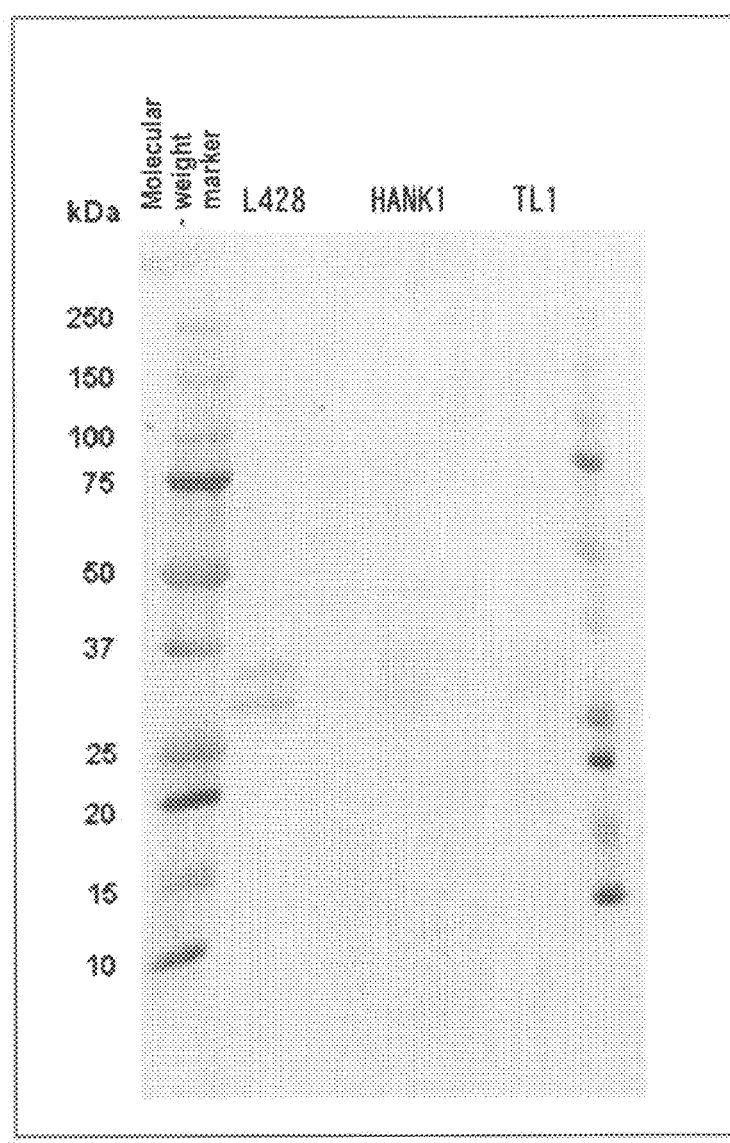
FIG. 11 is a diagram showing the reactivity of the monoclonal antibody of the present invention with degradation products of L428, HANKS, and TL-1.
Figure 12:
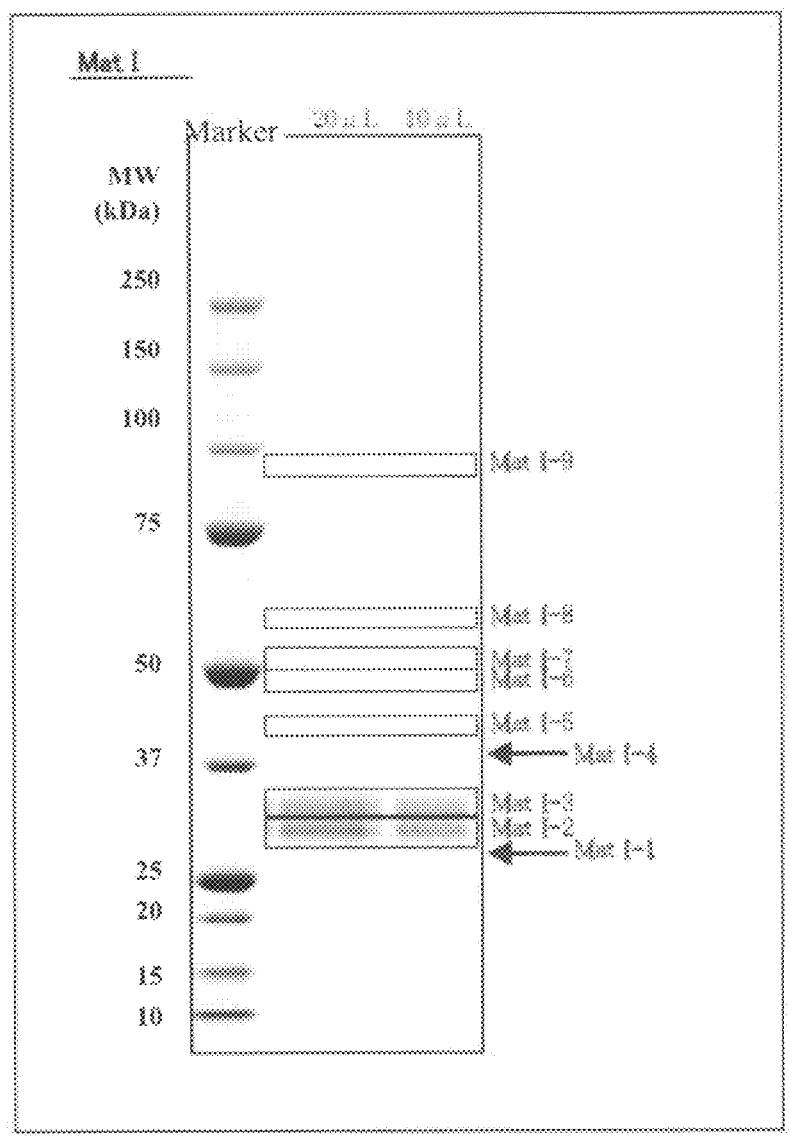
FIG. 12 shows results of PMF analysis on the L428 cell-derived elution fractions of the monoclonal antibody of the present invention.
Figure 13:
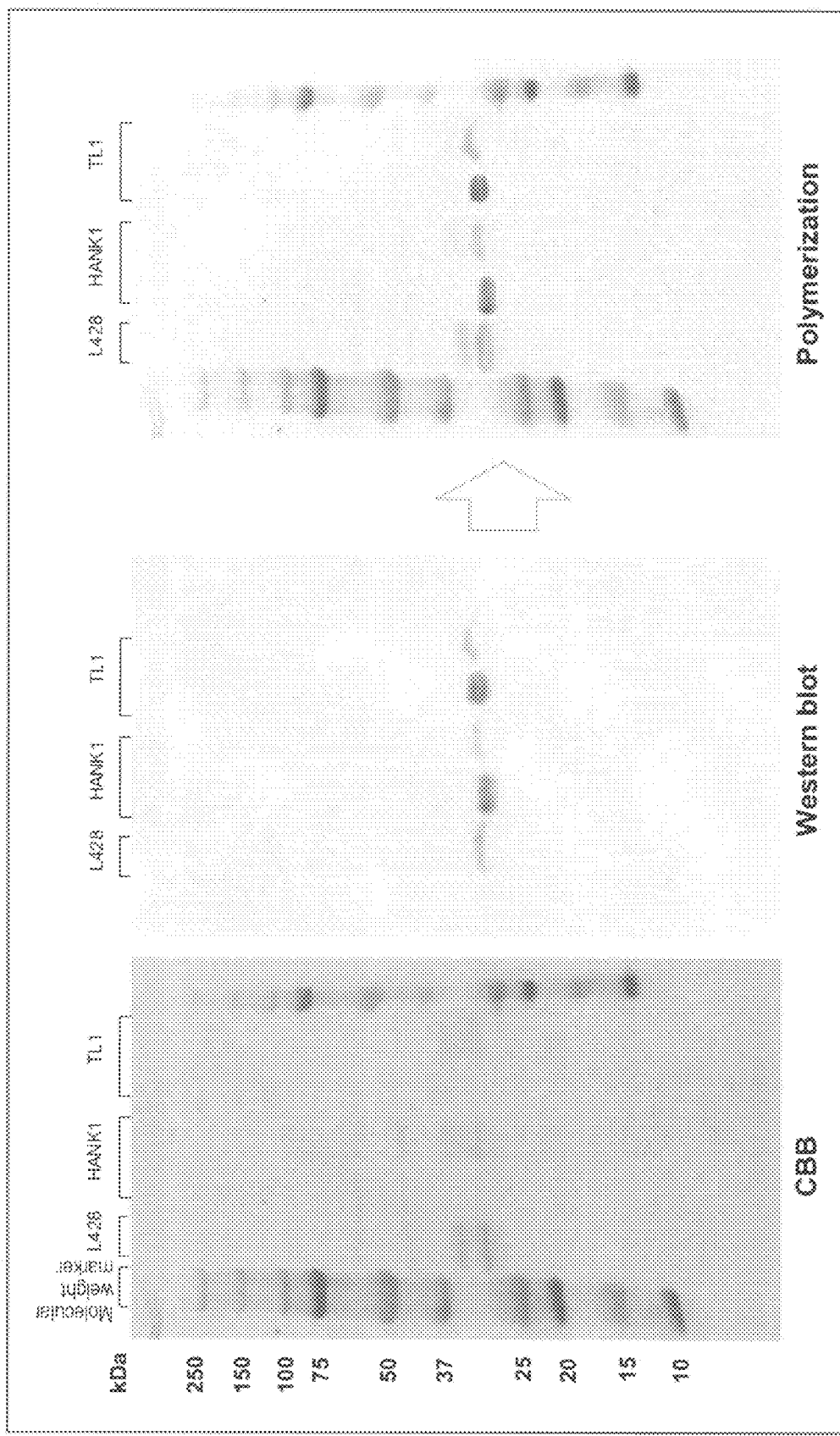
FIG. 13 is a diagram showing the reactivity of the monoclonal antibody of the present invention with degradation products of L428, HANKS, and TL-1.

The elution fractions were separated by SDS-polyacrylamide gel electrophoresis and stained with Coomassie brilliant blue (FIG. 11). L428 cell-derived elution fractions recovered at a high rate were numbered starting at 1 for the lowest molecular weight in order. Nine bands were analyzed by peptide mass fingerprint (PMF) (FIG. 12). The results are shown in Table 2 (this analysis was carried out by Shimadzu Techno-Research, Inc.). Next, the elution fractions were subjected to SDS-polyacrylamide gel electrophoresis and then analyzed by Western blot using 4713 mAb. As a result, 4713 mAb was confirmed to bind to the HLA-DR β chain corresponding to the band Mat I-2 identified by PMF analysis (FIG. 13).

TABLE 2

Mat I-9: Exportin-5, RANBP21
Mat I-8: TCP-1 subunit 8 (q)
Mat I-7: Tublin b-2C
Mat I-6: Keratin
Mat I-5: actin
Mat I-3: HLA-DR α-chain
Mat I-2: HLA-DR β-chain Example 11

Analysis of 4713 mAb for its Ability to Bind to Peptide Library of HLA Class II-β Chain Overlapping peptides consisting of 8 to 12 amino acids shifted by one amino acid were chemically synthesized from their C termini on an array using the amino acid sequence of an HLA-DR52 β chain having the highest homology as a result of analysis using software Mascot (Shimadzu Techno-Research, Inc.) to prepare a peptide microarray (LC Sciences, LLC, Texas, US). First, the array was blocked by immersion overnight at 4° C. in a SuperBlock (pH 7.0) (Pierce Biotechnology Inc.) solution containing 0.05% Tween-20 to prevent nonspecific antibody binding. Next, the array was washed with a phosphate buffer solution (pH 7.0) containing 0.05% Tween-20 and 0.05% Triton X-100 as a washing solution and then incubated at 25° C. for 1 hour in a 5 µg/mL 4713 mAb solution. The array was washed with the washing solution for 20 minutes and then incubated at 25° C. for 1 hour in a 10 ng/mL Cy5-labeled goat anti-mouse IgG antibody solution. Cy5 was assayed at a wavelength of 635 nm using a microarray scanner (PMT 700 V). Since nonspecific binding to a peptide sequence having a C-terminal tryptophan residue was observed, this sequence was omitted and peptide sequences showing specific binding were then analyzed. As a result, a 4713 mAb-specific binding signal was confirmed only in the region of a peptide (CRHNYGVGESFT: SEQ ID NO: 1) consisting of 12 amino acid residues starting at the second N-terminal cysteine residue among four cysteine residues conserved in all HLA class II (DR, DP, and DQ) β chain molecules. A peptide sequence (WNSQKDILEQKRG: SEQ ID NO: 2) of the HLA-DR β-chain to which an antibody described in WO2003/033538 bind is located 6 amino acid residues before the second N-terminal cysteine residue. The binding of 4713 mAb to this region was not seen.

In order to reconfirm the results obtained using the peptide microarray, HLA-DR expressed by L428 cells was analyzed. Results of serological typing demonstrated that L428 cells express only HLA-DR12 (SRL Inc.). Next, overlapping peptides were synthesized from the amino acid sequence of HLA-DR12 to prepare a custom SPOTs nitrocellulose membrane (Sigma-Aldrich Corp.). The membrane was rinsed with methanol for 5 minutes, then washed with a tris-borate buffer solution (TBS), and incubated at room temperature for 2 hours for blocking. Next, the biotinylated 4713 antibody was added thereto at a final concentration of 1 μg/mL and incubated for 3 hours. The membrane was washed and then incubated for 2 hours in a solution of peroxidase (HRP)-labeled streptavidin (manufactured by Dako Japan Inc.) diluted 3000-fold with TBS. After washing, positive spots were detected using ECL Prime Western Blotting Detection kit (manufactured by GE Healthcare Japan Corp.) and a chemiluminescence detector (LAS-4000) (Table 3). As a result, the most strongly reacted peptide was DR12-26, followed by DR12-6 and DR12-13. As a result of peptide microarray analysis, this DR12-13 was an HLA-DR12-derived peptide sequence having the same region as in the only one HLA-DR52 peptide sequence CRHNYGVGESFT to which 4713 mAb had the ability to specifically bind, demonstrating that this ability to bind was reproducible. Although an HLA-DR12-derived peptide to which the antibody described in WO2003/033538 binds was also arrayed as DR12-28, no binding was seen (Table 3). By contrast, the antibody also exhibited the ability to strongly bind to the DR12-26 peptide located in the intracellular region of HLA-DR and the DR12-6 peptide located in another extracellular region, suggesting the possibility that the 4713 antibody was also capable of binding to a peptide other than the epitope sequence.

TABLE 3

| HLA-DR12 | Peptide | Binding affinity |
|---|---|---|
| DR12-1 | MVCLKLPGGSSLAAL (SEQ ID NO 3) | − |
| DR12-2 | SSLAALTVTLMVLSS (SEQ ID NO 4) | + |
| DR12-3 | LMVLSSRLAFAGDTR (SEQ ID NO 5) | + |
| DR12-4 | FAGDTRPRFLEYSTG (SEQ ID NO 6) | + |
| DR12-5 | LEYSTGECYFFNGTE (SEQ ID NO 7) | − |
| DR12-6 | FFNGTERVRLLERHF (SEQ ID NO 8) | ++ |
| DR12-7 | LLERHFHNQEELLRF (SEQ ID NO 9) | + |
| DR12-8 | EELLRFDSDVGEFRA (SEQ ID NO 10) | − |
| DR12-9 | VGEFRAVTELGRPVA (SEQ ID NO 11) | − |
| DR12-10 | LGRPVAESWNSQKDI (SEQ ID NO 12) | − |
| DR12-11 | NSQKDILEDRRAAVD (SEQ ID NO 13) | − |
| DR12-12 | RRAAVDTYCRHNYGA (SEQ ID NO 14) | − |
| DR12-13 | RHNYGAVESFTVQRR (SEQ ID NO 15) | ++ |
| DR12-14 | FTVQRRVHPKVTVYP (SEQ ID NO 16) | + |
| DR12-15 | KVTVYPSKTQPLQHH (SEQ ID NO 17) | + |
| DR12-16 | QPLQHHNLLVCSVSG (SEQ ID NO 18) | − |
| DR12-17 | VCSVSGFYPGSIEVR (SEQ ID NO 19) | + |
| DR12-18 | GSIEVRWFRNGQEEK (SEQ ID NO 20) | − |
| DR12-19 | NGQEEKTGVVSTGLI (SEQ ID NO 21) | − |
| DR12-20 | VSTGLIQNGDWTFQT (SEQ ID NO 22) | − |
| DR12-21 | DWTFQTLVMLETVPR (SEQ ID NO 23) | − |
| DR12-22 | LETVPRSGEVYTCQV (SEQ ID NO 24) | − |

TABLE 3-continued

| HLA-DR12 | Peptide | Binding affinity |
|---|---|---|
| DR12-23 | VYTCQVEHPSVTSPL (SEQ ID NO 25) | − |
| DR12-24 | SVTSPLTVEWRARSE (SEQ ID NO 26) | − |
| DR12-25 | WRARSESAQSK (SEQ ID NO 27) | + |
| DR12-26 | RNQKGHSGLQPRGFLS (SEQ ID NO 28) | +++ |
| DR12-27 | WNSQKDFLEDRRA (SEQ ID NO 29) | − |
| DR12-28 | WNSQKDILEDRRA (SEQ ID NO 30) | − |

Example 12

Analysis of 4713 mAb for its Ability to Bind to HLA-DR Epitope Peptide Library

A peptide library of epitope sequences within the HLA-DR β chain to which the antibody described in WO2003/033538 binds was prepared on a custom SPOTs nitrocellulose membrane in the same way as in Example 11. The 4713 antibody was analyzed for its ability to bind thereto by Western blotting. As a result, the antibody was confirmed to have the ability to bind to peptides #25, #34, and #38 (Table 4). In addition, the ability of the antibody to bind to three peptides DR12-6, DR-12-13, and DR-12-26 confirmed in Example 11 was also confirmed to be reproducible. These results suggest the ability of the 4713 antibody to bind to a peptide sequence other than the epitope sequence. However, no homology was observed among the primary sequences of the bound peptide groups, indicating that the antibody may recognize the three-dimensional structures of the peptides.

TABLE 4

| | | Peptide | | Binding affinity |
|---|---|---|---|---|
| 1 | #24 | WNSQKDFLEDRRA (SEQ ID NO 31) | 13 | |
| 2 | #25 | WNSQKDFLERRRA (SEQ ID NO 32) | 13 | ++ |
| 3 | #26 | WNSQKDFLEDERA (SEQ ID NO 33) | 13 | |
| 4 | #27 | WNSQKDFLEQARA (SEQ ID NO 34) | 13 | |
| 5 | #28 | WNSQKDILEDERA (SEQ ID NO 35) | 13 | |
| 6 | #29 | WNSQKDILEQKRG (SEQ ID NO 36) | 13 | |
| 7 | #30 | WNSQKDILEDRRA (SEQ ID NO 37) | 13 | |
| 8 | #31 | WNSQKDILEDRRG (SEQ ID NO 38) | 13 | |
| 9 | #32 | WNSQKDILEDKRA (SEQ ID NO 39) | 13 | |
| 10 | #33 | WNSQKDILEQARA (SEQ ID NO 40) | 13 | |
| 11 | #34 | WNSQKDLLEQRRA (SEQ ID NO 41) | 13 | + |
| 12 | #35 | WNSQKDLLEQARA (SEQ ID NO 42) | 13 | |
| 13 | #36 | WNSQKDLLEQKRG (SEQ ID NO 43) | 13 | |
| 14 | #37 | WNSQKDLLEDRRA (SEQ ID NO 44) | 13 | |

TABLE 4-continued

|   | | Peptide | | Binding affinity |
|---|---|---|---|---|
| 15 | #38 | WNSQKDLLERRRA (SEQ ID NO 45) | 13 | + |
| 16 | #39 | WNSQKDLLEDERA (SEQ ID NO 46) | 13 | |
| 17 | #40 | WNSQKDALEQRRA (SEQ ID NO 47) | 13 | |
| 18 | #41 | WNSQKDLLEARRA (SEQ ID NO 48) | 13 | |
| 19 | #42 | WNSQKDLLEQARA (SEQ ID NO 49) | 13 | |
| 20 | #43 | WNSQKDLLEQRRG (SEQ ID NO 50) | 13 | |
| 21 | #83 | SQKDILEQARAV (SEQ ID NO 51) | 12 | |
| 22 | #84 | KDILEQARAVDT (SEQ ID NO 52) | 12 | |
| 23 | DR12-26 | RNQKGHSGLQPRGFLS (SEQ ID NO 28) | 16 | ++ |
| 24 | DR12-6 | FFNGTERVRLLERHF (SEQ ID NO 8) | 15 | ++ |
| 25 | DR12-13 | RHNYGAVESFTVQRR (SEQ ID NO 15) | 15 | + |

Example 13

Figure 14:
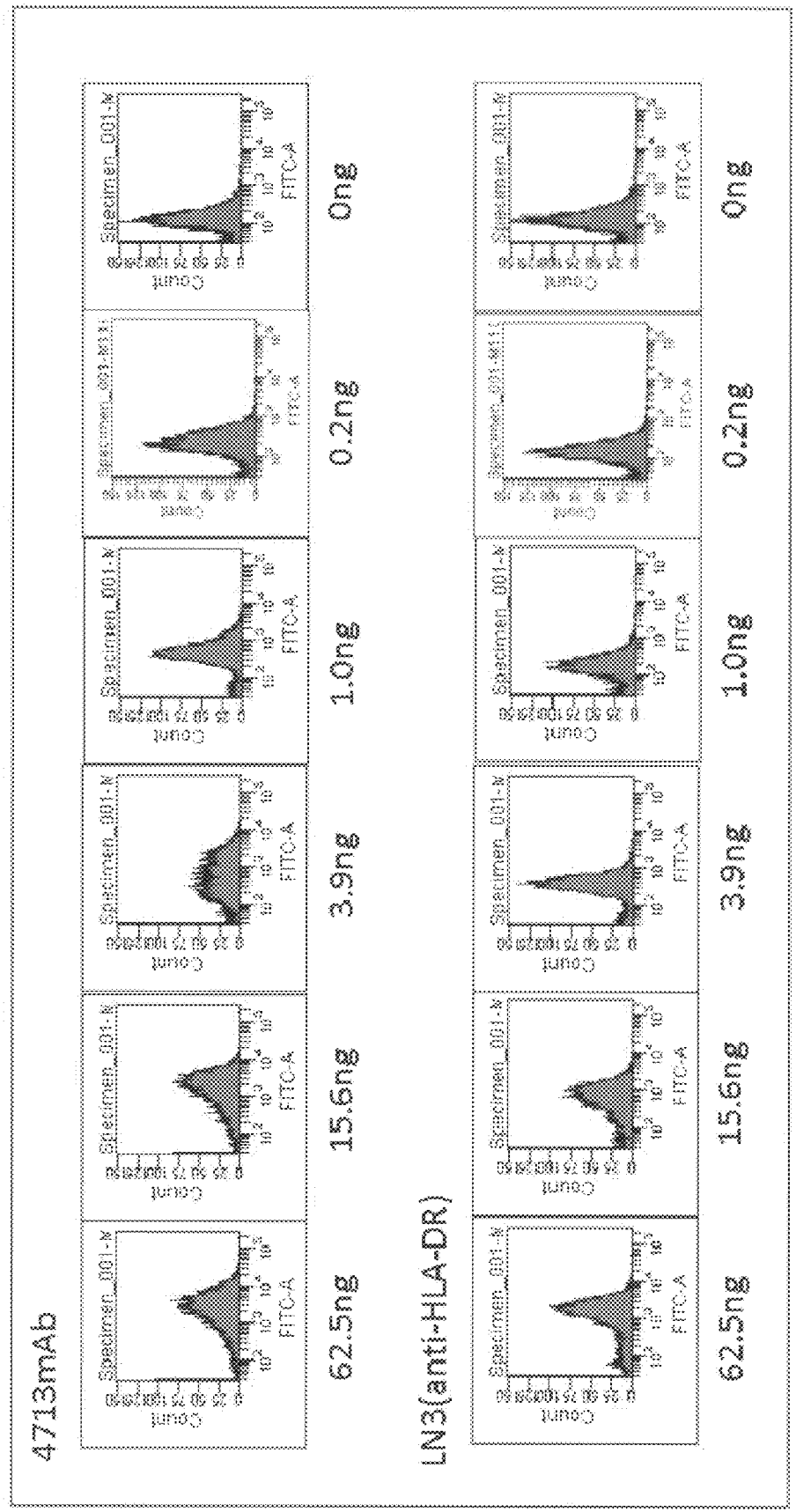
FIG. 14 shows the binding affinities of the monoclonal antibody of the present invention and a commercially available anti-HLA-DR antibody for L428 cells.

Comparison of Abilities of 4713 mAb and Anti-HLA-DR Antibody to Bind to L428 Cells and to Induce Cell Death The abilities to bind to L428 cells and to induce cell death were compared between 4713 mAb and a commercially available antibody (clone name: LN3) known to bind to HLA-DR, as well as 4713 mAb. The ability of each antibody to bind to L428 cells was analyzed by incubation with each of serially diluted antibody solutions using a flow cytometer. Both the antibodies exhibited the concentration-dependent ability to bind. 4713 mAb, however, was confirmed to exhibit the ability to bind at about 10 times lower concentration than LN3 (FIG. 14 and Table 5). For cell death induction, the uptake of propidium iodide (PI) was analyzed using a flow cytometer. As a result, the ability of 4713 mAb to induce cell death correlated with the ability to bind to cell surface and was active at about 10 times lower concentration than LN3 (Table 5).

TABLE 5

Concentration-dependent ability of 4713 antibody to bind to L428 cells and its ability to induce cell death

| | 4713mAb | | LN3 | |
|---|---|---|---|---|
| Antibody concentration (ng/mL) | Ability to bind (average strength) | Cell death (%) | Ability to bind (average strength) | Cell death (%) |
| 250.0 | 6993 | 86 (%) | 3274 | 77 (%) |
| 125.0 | 4118 | 85 (%) | 2419 | 72 (%) |
| 62.5 | 3366 | 77 (%) | 1613 | 68 (%) |
| 31.2 | 2629 | 72 (%) | 928 | 40 (%) |
| 15.6 | 2076 | 68 (%) | 694 | 35 (%) |
| 7.8 | 1434 | 66 (%) | 430 | 14 (%) |
| 3.9 | 942 | 35 (%) | 339 | 5 (%) |
| 1.95 | 645 | 32 (%) | 230 | 2 (%) |
| 0.98 | 497 | 16 (%) | 181 | 1 (%) |
| 0.0 | 129 | 1 (%) | 129 | 1 (%) |

Example 14

Cloning of Antibody Gene from 4713 mAb-Producing Hybridoma

1. Mouse Antibody (IgG) Sequence-Specific RT Reaction
Total RNA was prepared from the 4713 mAb-producing hybridoma (deposition No. FERM BP-11418) according to a standard method and used as a template to synthesize cDNA using a mouse antibody (IgG) heavy chain-specific primer (H-RT1: TCCAKAGTTCCA). Similarly, cDNA was synthesized using a light chain-specific primer (L-RT1: GCTGTC-CTGATC). RT reaction was performed according to the instruction of SMARTer™ RACE cDNA Amplification Kit (Clontech Cat. No. 634924) under the following conditions:
(1) 0.5 μg of total RNA, 1 μl of H-RT1 or L-RT1 (12 μM), and dH$_2$O up to 3.75 μl were mixed and reacted at 70° C. for 3 minutes and at 42° C. for 2 minutes.
(2) 1 μl of SMARTer II A Oligonucleotide (12 μM), 1 μl of DTT (20 mM), 1 μl of dNTP Mix (10 mM each), 2 μl of 5× First-Strand Buffer, 0.25 μl of RNase Inhibitor (40 U/μl), and 1 μl of SMARTScribe™ Reverse Transcriptase (100 U/μl) were added to the reaction solution and reacted at 42° C. for 90 minutes and at 70° C. for 10 minutes.
(3) The reaction was terminated by the addition of 50 μl of a tricine-EDTA buffer, and the solution was stored at −20° C.

2. Mouse Antibody (IgG) Sequence-Specific RACE PCR Reaction
5' RACE PCR analysis was conducted using SMARTer™ RACE cDNA Amplification Kit.
(1) RACE PCR reaction was performed with the cDNA (synthesized with the heavy chain-specific primer) synthesized in the paragraph 1 as a template using the mouse antibody (IgG) heavy chain-specific primer as a reverse primer and Universal primer mix (UPM) included in the kit as a forward primer. Similarly, RACE PCR reaction was performed with the cDNA (synthesized with the light chain-specific primer) as a template using the light chain-specific primer. The PCR enzyme used was PrimeSTAR (Takara Bio Inc.).
PCR reaction was performed according to the protocol included in the kit.
(2) The successful obtainment of PCR products of expected sizes was confirmed by electrophoresis on an agarose gel. The PCR products were designated as SYN3460H for H-chain RT-PCR and SYN3460L for L-chain RT-PCR, then purified by gel removal, and then used in analysis.

3. Cloning and Sequencing
(1) The PCR products (SYN3460H and SYN3460L) thus purified by gel removal were each ligated with cloning plasmids pMD20-T (Takara Bio Inc.).
(2) Transformation was performed according to a standard method to obtain 48 clones per PCR product.
(3) The insert contained in each clone thus obtained was sequenced according to a standard method. Sequencing reaction was performed using BigDye Terminators v3.1 Cycle Sequencing Kit (Applied Biosystems, Inc.) and ABI3730 Sequencer (Applied Biosystems, Inc.) according to the protocol thereof.
(4) The results of sequencing 48 clones each for the heavy and light chains and their nucleotide sequences except for the vector region and a low reliable region were obtained.

4. Evaluation of Results
Next, the following analysis was conducted using the nucleotide sequences obtained in the paragraph 3-(4):
(1) Classification of Obtained Sequences and Obtainment of Consensus Sequences
The nucleotide sequences of the heavy and light chains were classified on the basis of homology. Homology was compared using DNA sequence assembly software SEQUENCHER™ (Gene Codes: Windows (registered trademark) version). As a result, two contigs and three contigs were obtained for the heavy and light chains, respectively (some observed sequences did not constitute such a contig). Consensus sequences were obtained from the obtained contigs.

(2) Regarding Candidate Sequence of Gene of Interest

The consensus sequences and contig-free sequences were screened for the sequences of possible candidates of the genes of interest. In this context, all of sequences having, without a stop codon, a codon for a methionine residue upstream of an amino acid sequence encoded by the antibody constant region gene were selected.

(3) Prediction of Amino Acid Sequence

Of the candidate sequences, the respective major contigs of the heavy and light chains were likely to be the sequences of interest on the basis of the number of sequences constituting contigs and the presumable gene lengths of the obtained sequences. Thus, amino acid sequences encoded by the respective consensus sequences of the major contigs were defined as the amino acid sequences of the heavy and light chains.

The gene sequences and amino acid sequences of the 4713 mAb heavy and light chain variable regions obtained by the above method are shown in FIGS. 15 and 16, respectively. The gene sequence and amino acid sequence of the light chain variable region are shown in SEQ ID NOs: 53 and 54, respectively. The gene sequence and amino acid sequence of the heavy chain variable region are shown in SEQ ID NOs: 55 and 56, respectively. According to the numbering of Kabat et al. (Kabat, E. A., et al., Sequences of Proteins of Immunological Interest, 5th ed., 1991, Bethesda: US Dept. of Health and Human Services, PHS, NIH.), positions 1 to 18 in SEQ ID NO: 54 correspond to a leader sequence; positions 49 to 54 correspond to CDR1; positions 69 to 84 correspond to CDR2; and positions 117 to 128 correspond to CDR3. Likewise, positions 1 to 22 in SEQ ID NO: 56 correspond to a leader sequence; positions 46 to 55 correspond to CDR1; positions 71 to 77 correspond to CDR2; and positions 100 to 108 correspond to CDR3.

The invention claimed is:

1. An antibody recognizing a MHC class II protein expressed on a malignant tumor, the antibody comprising a light chain CDR1 (amino acid sequence represented by positions from 49 to 54 of SEQ ID NO: 54), a light chain CDR2 (amino acid sequence represented by positions from 69 to 84 of SEQ ID NO: 54), a light chain CDR3 (amino acid sequence represented by positions from 117 to 128 of SEQ ID NO: 54), a heavy chain CDR1 (amino acid sequence represented by in positions from 46 to 55 of SEQ ID NO: 56), a heavy chain CDR2 (amino acid sequence represented by positions from 71 to 77 of SEQ ID NO: 56), and a heavy chain CDR3 (amino acid sequence represented by positions from 100 to 108 of SEQ ID NO: 56).

2. The antibody according to claim 1, comprising:
a light chain having a light chain variable region comprising an amino acid sequence in positions from 19 to 143 of SEQ ID NO: 54,
wherein one or several amino acids within the framework region of the amino acid sequence of SEQ ID NO: 54 are optionally deleted, substituted, added, or a combination thereof.

3. The antibody according to claim 1, comprising:
a heavy chain having a heavy chain variable region comprising an amino acid sequence in positions from 23 to 132 of SEQ ID NO: 56
wherein one or several amino acids within the framework region of the amino acid sequence of SEQ ID NO: 56 are optionally deleted, substituted, added, or a combination thereof.

4. The antibody according to claim 1,
wherein the antibody has a specific cytotoxic activity against the malignant tumor.

5. The antibody according to claim 1,
wherein the malignant tumor expressing the MHC class II protein is malignant lymphoma.

6. The antibody according to claim 1,
wherein the MHC class II protein is at least one member selected from the group consisting of HLA-DPβ, HLA-DQβ, and HLA-DRβ.

7. The antibody according to claim 6,
wherein the MHC class II protein is HLA-DRβ.

8. A pharmaceutical composition, comprising:
the antibody according to claim 1.

9. A therapeutic agent, comprising:
the antibody according to claim 1 as an active ingredient,
wherein the therapeutic agent is suitable for the malignant tumor expressing the MHC class II protein.

10. A reagent, comprising:
the antibody according to claim 1,
wherein the reagent is suitable for detecting the malignant tumor expressing the MHC class II protein.

11. A method for treating the malignant tumor expressing the MHC class II protein, comprising:
administering an effective amount of the antibody according to claim 1 to a subject in need thereof.

* * * * *

SEQUENCE LISTING

```
<160> NUMBER OF SEQ ID NOS: 58

<210> SEQ ID NO 1
<211> LENGTH: 12
<212> TYPE: PRT
<213> ORGANISM: Artificial sequence
<220> FEATURE:
<223> OTHER INFORMATION: Designed peptide based on HLA class II beta-
      chain

<400> SEQUENCE: 1

Cys Arg His Asn Tyr Gly Val Gly Glu Ser Phe Thr
1               5                   10

<210> SEQ ID NO 2
<211> LENGTH: 13
<212> TYPE: PRT
<213> ORGANISM: Artificial sequence
<220> FEATURE:
<223> OTHER INFORMATION: Designed peptide based on HLA-DR beta-chain

<400> SEQUENCE: 2

Trp Asn Ser Gln Lys Asp Ile Leu Glu Gln Lys Arg Gly
1               5                   10

<210> SEQ ID NO 3
<211> LENGTH: 15
<212> TYPE: PRT
<213> ORGANISM: Artificial sequence
<220> FEATURE:
<223> OTHER INFORMATION: Designed peptide based on HLA-DR12

<400> SEQUENCE: 3

Met Val Cys Leu Lys Leu Pro Gly Gly Ser Ser Leu Ala Ala Leu
1               5                   10                  15

<210> SEQ ID NO 4
<211> LENGTH: 15
<212> TYPE: PRT
<213> ORGANISM: Artificial sequence
<220> FEATURE:
<223> OTHER INFORMATION: Designed peptide based on HLA-DR12

<400> SEQUENCE: 4
```

Ser Ser Leu Ala Ala Leu Thr Val Thr Leu Met Val Leu Ser Ser
1               5                   10                  15

<210> SEQ ID NO 5
<211> LENGTH: 15
<212> TYPE: PRT
<213> ORGANISM: Artificial sequence
<220> FEATURE:
<223> OTHER INFORMATION: Designed peptide based on HLA-DR12

<400> SEQUENCE: 5

Leu Met Val Leu Ser Ser Arg Leu Ala Phe Ala Gly Asp Thr Arg
1               5                   10                  15

<210> SEQ ID NO 6
<211> LENGTH: 15
<212> TYPE: PRT
<213> ORGANISM: Artificial sequence
<220> FEATURE:
<223> OTHER INFORMATION: Designed peptide based on HLA-DR12

<400> SEQUENCE: 6

Phe Ala Gly Asp Thr Arg Pro Arg Phe Leu Glu Tyr Ser Thr Gly
1               5                   10                  15

<210> SEQ ID NO 7
<211> LENGTH: 15
<212> TYPE: PRT
<213> ORGANISM: Artificial sequence
<220> FEATURE:
<223> OTHER INFORMATION: Designed peptide based on HLA-DR12

<400> SEQUENCE: 7

Leu Glu Tyr Ser Thr Gly Glu Cys Tyr Phe Phe Asn Gly Thr Glu
1               5                   10                  15

<210> SEQ ID NO 8
<211> LENGTH: 15
<212> TYPE: PRT
<213> ORGANISM: Artificial sequence
<220> FEATURE:
<223> OTHER INFORMATION: Designed peptide based on HLA-DR12

<400> SEQUENCE: 8

Phe Phe Asn Gly Thr Glu Arg Val Arg Leu Leu Glu Arg His Phe
1               5                   10                  15

<210> SEQ ID NO 9
<211> LENGTH: 15
<212> TYPE: PRT
<213> ORGANISM: Artificial sequence
<220> FEATURE:
<223> OTHER INFORMATION: Designed peptide based on HLA-DR12

<400> SEQUENCE: 9

Leu Leu Glu Arg His Phe His Asn Gln Glu Glu Leu Leu Arg Phe
1               5                   10                  15

<210> SEQ ID NO 10
<211> LENGTH: 15
<212> TYPE: PRT
<213> ORGANISM: Artificial sequence
<220> FEATURE:
<223> OTHER INFORMATION: Designed peptide based on HLA-DR12

<400> SEQUENCE: 10

Glu Glu Leu Leu Arg Phe Asp Ser Asp Val Gly Glu Phe Arg Ala

<210> SEQ ID NO 11
<211> LENGTH: 15
<212> TYPE: PRT
<213> ORGANISM: Artificial sequence
<220> FEATURE:
<223> OTHER INFORMATION: Designed peptide based on HLA-DR12

<400> SEQUENCE: 11

Val Gly Glu Phe Arg Ala Val Thr Glu Leu Gly Arg Pro Val Ala
1               5                   10                  15

<210> SEQ ID NO 12
<211> LENGTH: 15
<212> TYPE: PRT
<213> ORGANISM: Artificial sequence
<220> FEATURE:
<223> OTHER INFORMATION: Designed peptide based on HLA-DR12

<400> SEQUENCE: 12

Leu Gly Arg Pro Val Ala Glu Ser Trp Asn Ser Gln Lys Asp Ile
1               5                   10                  15

<210> SEQ ID NO 13
<211> LENGTH: 15
<212> TYPE: PRT
<213> ORGANISM: Artificial sequence
<220> FEATURE:
<223> OTHER INFORMATION: Designed peptide based on HLA-DR12

<400> SEQUENCE: 13

Asn Ser Gln Lys Asp Ile Leu Glu Asp Arg Arg Ala Ala Val Asp
1               5                   10                  15

<210> SEQ ID NO 14
<211> LENGTH: 15
<212> TYPE: PRT
<213> ORGANISM: Artificial sequence
<220> FEATURE:
<223> OTHER INFORMATION: Designed peptide based on HLA-DR12

<400> SEQUENCE: 14

Arg Arg Ala Ala Val Asp Thr Tyr Cys Arg His Asn Tyr Gly Ala
1               5                   10                  15

<210> SEQ ID NO 15
<211> LENGTH: 15
<212> TYPE: PRT
<213> ORGANISM: Artificial sequence
<220> FEATURE:
<223> OTHER INFORMATION: Designed peptide based on HLA-DR12

<400> SEQUENCE: 15

Arg His Asn Tyr Gly Ala Val Glu Ser Phe Thr Val Gln Arg Arg
1               5                   10                  15

<210> SEQ ID NO 16
<211> LENGTH: 15
<212> TYPE: PRT
<213> ORGANISM: Artificial sequence
<220> FEATURE:
<223> OTHER INFORMATION: Designed peptide based on HLA-DR12

<400> SEQUENCE: 16

Phe Thr Val Gln Arg Arg Val His Pro Lys Val Thr Val Tyr Pro
1               5                   10                  15

<210> SEQ ID NO 17
<211> LENGTH: 15
<212> TYPE: PRT
<213> ORGANISM: Artificial sequence
<220> FEATURE:
<223> OTHER INFORMATION: Designed peptide based on HLA-DR12

<400> SEQUENCE: 17

Lys Val Thr Val Tyr Pro Ser Lys Thr Gln Pro Leu Gln His His
1               5                   10                  15

<210> SEQ ID NO 18
<211> LENGTH: 15
<212> TYPE: PRT
<213> ORGANISM: Artificial sequence
<220> FEATURE:
<223> OTHER INFORMATION: Designed peptide based on HLA-DR12

<400> SEQUENCE: 18

Gln Pro Leu Gln His His Asn Leu Leu Val Cys Ser Val Ser Gly
1               5                   10                  15

<210> SEQ ID NO 19
<211> LENGTH: 15
<212> TYPE: PRT
<213> ORGANISM: Artificial sequence
<220> FEATURE:
<223> OTHER INFORMATION: Designed peptide based on HLA-DR12

<400> SEQUENCE: 19

Val Cys Ser Val Ser Gly Phe Tyr Pro Gly Ser Ile Glu Val Arg
1               5                   10                  15

<210> SEQ ID NO 20
<211> LENGTH: 15
<212> TYPE: PRT
<213> ORGANISM: Artificial sequence
<220> FEATURE:
<223> OTHER INFORMATION: Designed peptide based on HLA-DR12

<400> SEQUENCE: 20

Gly Ser Ile Glu Val Arg Trp Phe Arg Asn Gly Gln Glu Glu Lys
1               5                   10                  15

<210> SEQ ID NO 21
<211> LENGTH: 15
<212> TYPE: PRT
<213> ORGANISM: Artificial sequence
<220> FEATURE:
<223> OTHER INFORMATION: Designed peptide based on HLA-DR12

<400> SEQUENCE: 21

Asn Gly Gln Glu Glu Lys Thr Gly Val Val Ser Thr Gly Leu Ile
1               5                   10                  15

<210> SEQ ID NO 22
<211> LENGTH: 15
<212> TYPE: PRT
<213> ORGANISM: Artificial sequence
<220> FEATURE:
<223> OTHER INFORMATION: Designed peptide based on HLA-DR12

<400> SEQUENCE: 22

Val Ser Thr Gly Leu Ile Gln Asn Gly Asp Trp Thr Phe Gln Thr
1               5                   10                  15

<210> SEQ ID NO 23
<211> LENGTH: 15
<212> TYPE: PRT
<213> ORGANISM: Artificial sequence
<220> FEATURE:
<223> OTHER INFORMATION: Designed peptide based on HLA-DR12

<400> SEQUENCE: 23

Asp Trp Thr Phe Gln Thr Leu Val Met Leu Glu Thr Val Pro Arg
1               5                   10                  15

<210> SEQ ID NO 24
<211> LENGTH: 15
<212> TYPE: PRT
<213> ORGANISM: Artificial sequence
<220> FEATURE:
<223> OTHER INFORMATION: Designed peptide based on HLA-DR12

<400> SEQUENCE: 24

Leu Glu Thr Val Pro Arg Ser Gly Glu Val Tyr Thr Cys Gln Val
1               5                   10                  15

<210> SEQ ID NO 25
<211> LENGTH: 15
<212> TYPE: PRT
<213> ORGANISM: Artificial sequence
<220> FEATURE:
<223> OTHER INFORMATION: Designed peptide based on HLA-DR12

<400> SEQUENCE: 25

Val Tyr Thr Cys Gln Val Glu His Pro Ser Val Thr Ser Pro Leu
1               5                   10                  15

<210> SEQ ID NO 26
<211> LENGTH: 15
<212> TYPE: PRT
<213> ORGANISM: Artificial sequence
<220> FEATURE:
<223> OTHER INFORMATION: Designed peptide based on HLA-DR12

<400> SEQUENCE: 26

Ser Val Thr Ser Pro Leu Thr Val Glu Trp Arg Ala Arg Ser Glu
1               5                   10                  15

<210> SEQ ID NO 27
<211> LENGTH: 11
<212> TYPE: PRT
<213> ORGANISM: Artificial sequence
<220> FEATURE:
<223> OTHER INFORMATION: Designed peptide based on HLA-DR12

<400> SEQUENCE: 27

Trp Arg Ala Arg Ser Glu Ser Ala Gln Ser Lys
1               5                   10

<210> SEQ ID NO 28
<211> LENGTH: 16
<212> TYPE: PRT
<213> ORGANISM: Artificial sequence
<220> FEATURE:
<223> OTHER INFORMATION: Designed peptide based on HLA-DR12

<400> SEQUENCE: 28

Arg Asn Gln Lys Gly His Ser Gly Leu Gln Pro Arg Gly Phe Leu Ser
1               5                   10                  15

```
<210> SEQ ID NO 29
<211> LENGTH: 13
<212> TYPE: PRT
<213> ORGANISM: Artificial sequence
<220> FEATURE:
<223> OTHER INFORMATION: Designed peptide based on HLA-DR12

<400> SEQUENCE: 29

Trp Asn Ser Gln Lys Asp Phe Leu Glu Asp Arg Arg Ala
1               5                   10

<210> SEQ ID NO 30
<211> LENGTH: 13
<212> TYPE: PRT
<213> ORGANISM: Artificial sequence
<220> FEATURE:
<223> OTHER INFORMATION: Designed peptide based on HLA-DR12

<400> SEQUENCE: 30

Trp Asn Ser Gln Lys Asp Ile Leu Glu Asp Arg Arg Ala
1               5                   10

<210> SEQ ID NO 31
<211> LENGTH: 13
<212> TYPE: PRT
<213> ORGANISM: Artificial sequence
<220> FEATURE:
<223> OTHER INFORMATION: Designed peptide based on HLA-DR12

<400> SEQUENCE: 31

Trp Asn Ser Gln Lys Asp Phe Leu Glu Asp Arg Arg Ala
1               5                   10

<210> SEQ ID NO 32
<211> LENGTH: 13
<212> TYPE: PRT
<213> ORGANISM: Artificial sequence
<220> FEATURE:
<223> OTHER INFORMATION: Designed peptide based on HLA-DR12

<400> SEQUENCE: 32

Trp Asn Ser Gln Lys Asp Phe Leu Glu Arg Arg Arg Ala
1               5                   10

<210> SEQ ID NO 33
<211> LENGTH: 13
<212> TYPE: PRT
<213> ORGANISM: Artificial sequence
<220> FEATURE:
<223> OTHER INFORMATION: Designed peptide based on HLA-DR12

<400> SEQUENCE: 33

Trp Asn Ser Gln Lys Asp Phe Leu Glu Asp Glu Arg Ala
1               5                   10

<210> SEQ ID NO 34
<211> LENGTH: 13
<212> TYPE: PRT
<213> ORGANISM: Artificial sequence
<220> FEATURE:
<223> OTHER INFORMATION: Designed peptide based on HLA-DR12

<400> SEQUENCE: 34

Trp Asn Ser Gln Lys Asp Phe Leu Glu Gln Ala Arg Ala
1               5                   10

<210> SEQ ID NO 35
```

```
<211> LENGTH: 13
<212> TYPE: PRT
<213> ORGANISM: Artificial sequence
<220> FEATURE:
<223> OTHER INFORMATION: Designed peptide based on HLA-DR12

<400> SEQUENCE: 35

Trp Asn Ser Gln Lys Asp Ile Leu Glu Asp Glu Arg Ala
1               5                   10

<210> SEQ ID NO 36
<211> LENGTH: 13
<212> TYPE: PRT
<213> ORGANISM: Artificial sequence
<220> FEATURE:
<223> OTHER INFORMATION: Designed peptide based on HLA-DR12

<400> SEQUENCE: 36

Trp Asn Ser Gln Lys Asp Ile Leu Glu Gln Lys Arg Gly
1               5                   10

<210> SEQ ID NO 37
<211> LENGTH: 13
<212> TYPE: PRT
<213> ORGANISM: Artificial sequence
<220> FEATURE:
<223> OTHER INFORMATION: Designed peptide based on HLA-DR12

<400> SEQUENCE: 37

Trp Asn Ser Gln Lys Asp Ile Leu Glu Asp Arg Arg Ala
1               5                   10

<210> SEQ ID NO 38
<211> LENGTH: 13
<212> TYPE: PRT
<213> ORGANISM: Artificial sequence
<220> FEATURE:
<223> OTHER INFORMATION: Designed peptide based on HLA-DR12

<400> SEQUENCE: 38

Trp Asn Ser Gln Lys Asp Ile Leu Glu Asp Arg Arg Gly
1               5                   10

<210> SEQ ID NO 39
<211> LENGTH: 13
<212> TYPE: PRT
<213> ORGANISM: Artificial sequence
<220> FEATURE:
<223> OTHER INFORMATION: Designed peptide based on HLA-DR12

<400> SEQUENCE: 39

Trp Asn Ser Gln Lys Asp Ile Leu Glu Asp Lys Arg Ala
1               5                   10

<210> SEQ ID NO 40
<211> LENGTH: 13
<212> TYPE: PRT
<213> ORGANISM: Artificial sequence
<220> FEATURE:
<223> OTHER INFORMATION: Designed peptide based on HLA-DR12

<400> SEQUENCE: 40

Trp Asn Ser Gln Lys Asp Ile Leu Glu Gln Ala Arg Ala
1               5                   10

<210> SEQ ID NO 41
<211> LENGTH: 13
```

<212> TYPE: PRT
<213> ORGANISM: Artificial sequence
<220> FEATURE:
<223> OTHER INFORMATION: Designed peptide based on HLA-DR12

<400> SEQUENCE: 41

Trp Asn Ser Gln Lys Asp Leu Leu Glu Gln Arg Arg Ala
1               5                   10

<210> SEQ ID NO 42
<211> LENGTH: 13
<212> TYPE: PRT
<213> ORGANISM: Artificial sequence
<220> FEATURE:
<223> OTHER INFORMATION: Designed peptide based on HLA-DR12

<400> SEQUENCE: 42

Trp Asn Ser Gln Lys Asp Leu Leu Glu Gln Ala Arg Ala
1               5                   10

<210> SEQ ID NO 43
<211> LENGTH: 13
<212> TYPE: PRT
<213> ORGANISM: Artificial sequence
<220> FEATURE:
<223> OTHER INFORMATION: Designed peptide based on HLA-DR12

<400> SEQUENCE: 43

Trp Asn Ser Gln Lys Asp Leu Leu Glu Gln Lys Arg Gly
1               5                   10

<210> SEQ ID NO 44
<211> LENGTH: 13
<212> TYPE: PRT
<213> ORGANISM: Artificial sequence
<220> FEATURE:
<223> OTHER INFORMATION: Designed peptide based on HLA-DR12

<400> SEQUENCE: 44

Trp Asn Ser Gln Lys Asp Leu Leu Glu Asp Arg Arg Ala
1               5                   10

<210> SEQ ID NO 45
<211> LENGTH: 13
<212> TYPE: PRT
<213> ORGANISM: Artificial sequence
<220> FEATURE:
<223> OTHER INFORMATION: Designed peptide based on HLA-DR12

<400> SEQUENCE: 45

Trp Asn Ser Gln Lys Asp Leu Leu Glu Arg Arg Arg Ala
1               5                   10

<210> SEQ ID NO 46
<211> LENGTH: 13
<212> TYPE: PRT
<213> ORGANISM: Artificial sequence
<220> FEATURE:
<223> OTHER INFORMATION: Designed peptide based on HLA-DR12

<400> SEQUENCE: 46

Trp Asn Ser Gln Lys Asp Leu Leu Glu Asp Glu Arg Ala
1               5                   10

<210> SEQ ID NO 47
<211> LENGTH: 13
<212> TYPE: PRT

<210> SEQ ID NO 47 (continued)
<213> ORGANISM: Artificial sequence
<220> FEATURE:
<223> OTHER INFORMATION: Designed peptide based on HLA-DR12

<400> SEQUENCE: 47

Trp Asn Ser Gln Lys Asp Ala Leu Glu Gln Arg Arg Ala
1               5                   10

<210> SEQ ID NO 48
<211> LENGTH: 13
<212> TYPE: PRT
<213> ORGANISM: Artificial sequence
<220> FEATURE:
<223> OTHER INFORMATION: Designed peptide based on HLA-DR12

<400> SEQUENCE: 48

Trp Asn Ser Gln Lys Asp Leu Leu Glu Ala Arg Arg Ala
1               5                   10

<210> SEQ ID NO 49
<211> LENGTH: 13
<212> TYPE: PRT
<213> ORGANISM: Artificial sequence
<220> FEATURE:
<223> OTHER INFORMATION: Designed peptide based on HLA-DR12

<400> SEQUENCE: 49

Trp Asn Ser Gln Lys Asp Leu Leu Glu Gln Ala Arg Ala
1               5                   10

<210> SEQ ID NO 50
<211> LENGTH: 13
<212> TYPE: PRT
<213> ORGANISM: Artificial sequence
<220> FEATURE:
<223> OTHER INFORMATION: Designed peptide based on HLA-DR12

<400> SEQUENCE: 50

Trp Asn Ser Gln Lys Asp Leu Leu Glu Gln Arg Arg Gly
1               5                   10

<210> SEQ ID NO 51
<211> LENGTH: 12
<212> TYPE: PRT
<213> ORGANISM: Artificial sequence
<220> FEATURE:
<223> OTHER INFORMATION: Designed peptide based on HLA-DR12

<400> SEQUENCE: 51

Ser Gln Lys Asp Ile Leu Glu Gln Ala Arg Ala Val
1               5                   10

<210> SEQ ID NO 52
<211> LENGTH: 12
<212> TYPE: PRT
<213> ORGANISM: Artificial sequence
<220> FEATURE:
<223> OTHER INFORMATION: Designed peptide based on HLA-DR12

<400> SEQUENCE: 52

Lys Asp Ile Leu Glu Gln Ala Arg Ala Val Asp Thr
1               5                   10

<210> SEQ ID NO 53
<211> LENGTH: 523
<212> TYPE: DNA
<213> ORGANISM: Mus musculus

<400> SEQUENCE: 53

```
atggattttc aagtgcagat tttcagcttc ctgctaatca gtgcctcagt caaaatttcc      60
agaggacaaa ttgttctcac ccagtctcca ccaatcatgt ctgcatctcc aggggagaag     120
gtcaccatga cctgcagtgc cagttcaagt gtaaattata tgcactggca ccagcagaag     180
tcaggcacct cccccaaaaa atggatttat gacacatcca aactgatttc tggagtccct     240
gctcgcttca gtggcagtgg gtctgggacc tcttactctc tcacaatcag cagcgtggag     300
gctgaagatg ctgccactta ttactgccag cagtggagca gttacccatt cacgttcggc     360
tcggggacaa agttggaaat aaacgggct gatgctgcac caactgtatc catcttccca     420
ccatccagtg agcagttaac atctggaggt gcctcagtcg tgtgcttctt gaacaacttc     480
tacccaaaag acatcaatgt caagtggaag attgatggca gtg                      523
```

<210> SEQ ID NO 54
<211> LENGTH: 174
<212> TYPE: PRT
<213> ORGANISM: Mus musculus

<400> SEQUENCE: 54

```
Met Asp Phe Gln Val Gln Ile Phe Ser Phe Leu Leu Ile Ser Ala Ser
1               5                   10                  15
Val Lys Ile Ser Arg Gly Gln Ile Val Leu Thr Gln Ser Pro Pro Ile
            20                  25                  30
Met Ser Ala Ser Pro Gly Glu Lys Val Thr Met Thr Cys Ser Ala Ser
        35                  40                  45
Ser Ser Val Asn Tyr Met His Trp His Gln Gln Lys Ser Gly Thr Ser
    50                  55                  60
Pro Lys Lys Trp Ile Tyr Asp Thr Ser Lys Leu Ile Ser Gly Val Pro
65                  70                  75                  80
Ala Arg Phe Ser Gly Ser Gly Ser Gly Thr Ser Tyr Ser Leu Thr Ile
                85                  90                  95
Ser Ser Val Glu Ala Glu Asp Ala Ala Thr Tyr Tyr Cys Gln Gln Trp
            100                 105                 110
Ser Ser Tyr Pro Phe Thr Phe Gly Ser Gly Thr Lys Leu Glu Ile Lys
        115                 120                 125
Arg Ala Asp Ala Ala Pro Thr Val Ser Ile Phe Pro Pro Ser Ser Glu
    130                 135                 140
Gln Leu Thr Ser Gly Gly Ala Ser Val Val Cys Phe Leu Asn Asn Phe
145                 150                 155                 160
Tyr Pro Lys Asp Ile Asn Val Lys Trp Lys Ile Asp Gly Ser
                165                 170
```

<210> SEQ ID NO 55
<211> LENGTH: 518
<212> TYPE: DNA
<213> ORGANISM: Mus musculus

<400> SEQUENCE: 55

```
atgagagtgc tgactctttt gtggctgttc acagcctttc tggtatcct gtctgatgtg      60
cagcttcagg agtcgggacc tggcctggtg aaaccttctc agtctctgtc cctcacctgc     120
actgtcactg gctactcaat caccaatgat tatgcctgga actggatccg gcagtttcca     180
ggaaacaaac tggagtggat gggctacata agctacaatg attcactta ctacaaccca     240
tctctcaaaa gtcgaatctc tatcactcgc gacacatcta agaaccagtt cttcctgcag     300
```

```
ttgaattctg tgactgccga ggacacagcc acttactact gtgtaagtga gaggcttcgc    360
ttagtaaacc atgttatgga ctactggggt cagggaacct cagtcatcgt ctcctcagcc    420
aaaacgacac ccccatctgt ctatccactg gccctggat ctgctgccca aactaactcc     480
atggtgaccc tgggatgcct tgtcaaaggc tatttccc                            518
```

<210> SEQ ID NO 56
<211> LENGTH: 172
<212> TYPE: PRT
<213> ORGANISM: Mus musculus

<400> SEQUENCE: 56

```
Met Arg Val Leu Thr Leu Leu Trp Leu Phe Thr Ala Phe Pro Gly Ile
1               5                   10                  15

Leu Ser Asp Val Gln Leu Gln Glu Ser Gly Pro Gly Leu Val Lys Pro
            20                  25                  30

Ser Gln Ser Leu Ser Leu Thr Cys Thr Val Thr Gly Tyr Ser Ile Thr
        35                  40                  45

Asn Asp Tyr Ala Trp Asn Trp Ile Arg Gln Phe Pro Gly Asn Lys Leu
    50                  55                  60

Glu Trp Met Gly Tyr Ile Ser Tyr Asn Asp Phe Thr Tyr Tyr Asn Pro
65                  70                  75                  80

Ser Leu Lys Ser Arg Ile Ser Ile Thr Arg Asp Thr Ser Lys Asn Gln
                85                  90                  95

Phe Phe Leu Gln Leu Asn Ser Val Thr Ala Glu Asp Thr Ala Thr Tyr
            100                 105                 110

Tyr Cys Val Ser Glu Arg Leu Arg Leu Val Asn His Val Met Asp Tyr
        115                 120                 125

Trp Gly Gln Gly Thr Ser Val Ile Val Ser Ser Ala Lys Thr Thr Pro
    130                 135                 140

Pro Ser Val Tyr Pro Leu Ala Pro Gly Ser Ala Ala Gln Thr Asn Ser
145                 150                 155                 160

Met Val Thr Leu Gly Cys Leu Val Lys Gly Tyr Phe
                165                 170
```

<210> SEQ ID NO 57
<211> LENGTH: 12
<212> TYPE: DNA
<213> ORGANISM: Artificial Sequence
<220> FEATURE:
<223> OTHER INFORMATION: Synthetic primer H-RT1

<400> SEQUENCE: 57

```
tccakagttc ca                                                        12
```

<210> SEQ ID NO 58
<211> LENGTH: 12
<212> TYPE: DNA
<213> ORGANISM: Artificial Sequence
<220> FEATURE:
<223> OTHER INFORMATION: Synthetic primer L-RT1

<400> SEQUENCE: 58

```
gctgtcctga tc                                                        12
```